(12) United States Patent
Miyawaki et al.

(10) Patent No.: US 10,030,055 B2
(45) Date of Patent: Jul. 24, 2018

(54) POLYPEPTIDE EXHIBITING FLUORESCENT PROPERTIES, AND UTILIZATION OF THE SAME

(71) Applicant: RIKEN, Wako-shi, Saitama (JP)

(72) Inventors: Atsushi Miyawaki, Wako (JP); Ryoko Ando, Wako (JP)

(73) Assignee: RIKEN, Saitama (JP)

( * ) Notice: Subject to any disclaimer, the term of this patent is extended or adjusted under 35 U.S.C. 154(b) by 61 days.

(21) Appl. No.: 14/913,483

(22) PCT Filed: Aug. 22, 2014

(86) PCT No.: PCT/JP2014/072039
§ 371 (c)(1),
(2) Date: Jun. 3, 2016

(87) PCT Pub. No.: WO2015/025959
PCT Pub. Date: Feb. 26, 2015

(65) Prior Publication Data
US 2016/0280746 A1  Sep. 29, 2016

(30) Foreign Application Priority Data

Aug. 23, 2013 (JP) ................................ 2013-173850

(51) Int. Cl.
| | |
|---|---|
| *A61K 48/00* | (2006.01) |
| *C07H 21/04* | (2006.01) |
| *C07K 14/00* | (2006.01) |
| *C12N 15/00* | (2006.01) |
| *C07K 14/435* | (2006.01) |
| *G01N 33/58* | (2006.01) |
| *C12N 15/79* | (2006.01) |

(52) U.S. Cl.
CPC ......... *C07K 14/435* (2013.01); *G01N 33/582* (2013.01); *C07H 21/04* (2013.01); *C07K 2319/60* (2013.01); *C12N 15/79* (2013.01); *C12N 2510/00* (2013.01)

(58) Field of Classification Search
CPC .. C07H 21/04; C07K 14/435; C07K 2319/60; C12N 15/79; C12N 2510/00; G01N 33/582
USPC ................... 424/93.21; 435/320.1; 530/350; 536/23.5
See application file for complete search history.

(56) References Cited

U.S. PATENT DOCUMENTS

| | | | |
|---|---|---|---|
| 5,491,084 A | 2/1996 | Chalfie et al. | |
| 5,882,893 A * | 3/1999 | Goodearl ......... | C07K 14/70571 435/252.3 |
| 7,067,278 B1 | 6/2006 | Hoech-Guldberg | |
| 7,166,444 B2 | 1/2007 | Lukyanov et al. | |
| 2006/0183133 A1* | 8/2006 | Matz et al. | |
| 2009/0170073 A1 | 7/2009 | Miyawaki et al. | |
| 2013/0267030 A1 | 10/2013 | Yamanaka et al. | |
| 2014/0106392 A1 | 4/2014 | Pasquier et al. | |

FOREIGN PATENT DOCUMENTS

| | | |
|---|---|---|
| JP | 2002-535978 | 10/2002 |
| WO | 00/46233 | 8/2000 |
| WO | 2004/111235 A1 | 12/2004 |
| WO | 2012/074117 A1 | 6/2012 |
| WO | 2012/172095 A1 | 12/2012 |

OTHER PUBLICATIONS

Matz et al., 2006, Geneseq Accession No. AEJ45899, computer printout, pp. 15-16.*
Search report for EP 14838441.5 dated Jun. 7, 2017.
Simone Kredel, et al; PLoS ONE. 2009; 4(2): e4391.
S Ekaterina M Merzlyak, et al; Nature Methods. 2007; 4, p. 555-557.
Shaner NC, at el; Nature Biotechnology. 2004; 22(12):p. 1567-1572.EpubNov. 21, 2004.
Griesbeck Oliver et al., Reducing the Environmental Sensitivity of Yellow Fluorescent Protein, The Journal of Biological Chemistry, 2001, vol. 276, No. 31, p. 29188-29194.
Alieva Naila O. et al, Diversity and Evolution of Coral Fluorescent Proteins, PLOS ONE, 2008, vol. 3, p. 1-12.
Porites porites red fluorescent GFP-like protein mRNA, complete cds Accession No. DQ206380, [online], NCBI, 2008, [retrieved on Nov. 12, 2014].
International Preliminary Report for PCT/JP2014/072039, dated Mar. 3, 2016.
International Search Report for PCT/JP2014/072039, dated Nov. 25, 2014.

* cited by examiner

*Primary Examiner* — Shin Lin Chen

(74) *Attorney, Agent, or Firm* — Kristina Castellano; Castellano PLLC

(57) ABSTRACT

A mode of a polypeptide according to the present invention exhibits a fluorescence property, and has (1) an amino acid sequence represented by SEQ ID NO. 1 or NO. 2, (2) an amino acid sequence represented by SEQ ID NO. 1 or NO. 2 in which amino acid sequence 1 to 34 amino acids have been replaced or otherwise modified, (3) a sequence identity of 85% or more with respect to the amino acid sequence represented by SEQ ID NO. 1 or NO. 2, or (4) an amino acid sequence encoded by a polynucleotide that hybridizes under a stringent condition with a polynucleotide having a sequence complementary to a polynucleotide that encodes the polypeptide defined in (1).

13 Claims, 17 Drawing Sheets

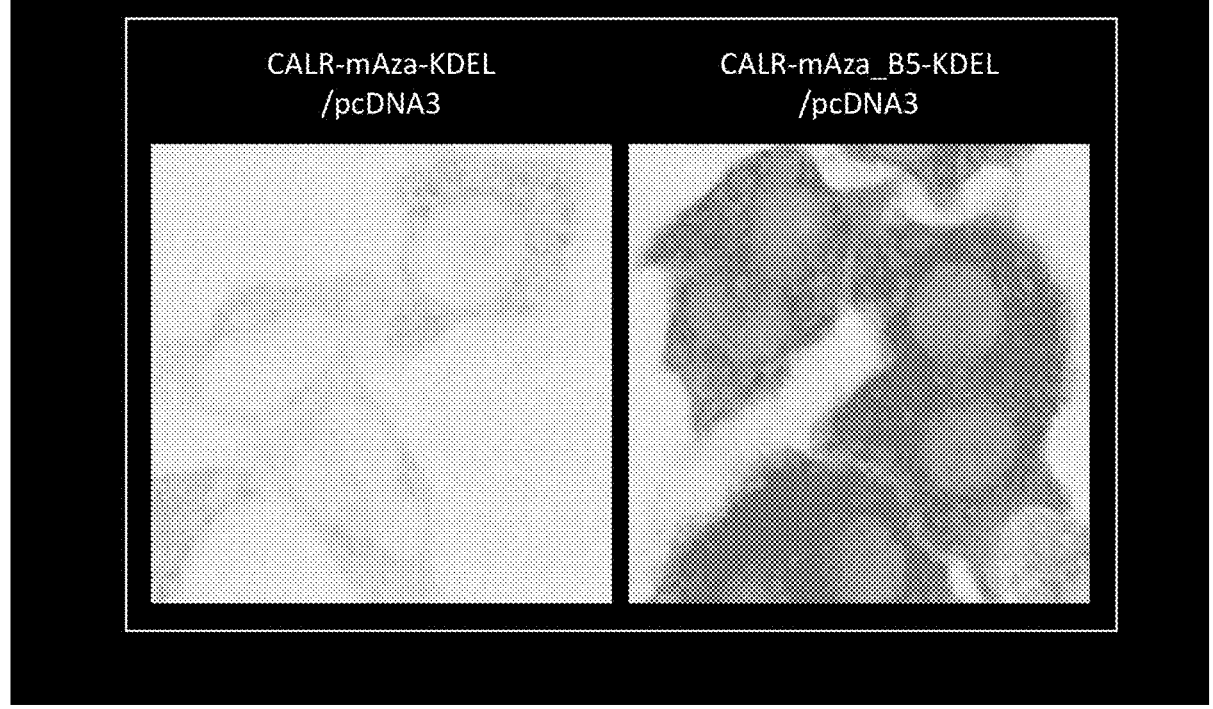

```
SEQUENCE LISTING

<160> NUMBER OF SEQ ID NOS: 19

<210> SEQ ID NO 1
<211> LENGTH: 230
<212> TYPE: PRT
<213> ORGANISM: Artificial Sequence
<220> FEATURE:
<223> OTHER INFORMATION: Mutant polypeptide having  fluorescent property

<400> SEQUENCE: 1

Met Glu Asn Val Arg Arg Lys Ser Gly Ile Gln Thr Glu Met Lys Thr
1               5                   10                  15

Lys Leu His Met Asp Gly Met Val Asn Gly His Ser Phe Glu Ile Lys
            20                  25                  30

Gly Glu Gly Lys Gly Ser Pro Tyr Glu Gly Val Gln Thr Met Lys Leu
        35                  40                  45

Lys Val Thr Lys Gly Ala Pro Leu Pro Phe Ser Ile Asp Ile Leu Leu
    50                  55                  60

Pro Gln Cys Met Tyr Gly Ser Lys Pro Phe Ile Lys Tyr Pro Glu Asn
65                  70                  75                  80

Ile Pro Asp Tyr Ile Lys Leu Ser Phe Pro Glu Gly Ile Thr Trp Glu
                85                  90                  95

Arg Thr Met Thr Phe Glu Asp Gly Ala Val Cys Asp Val Ser Asn Asp
            100                 105                 110

Ser Arg Leu Val Gly Asn Cys Phe Asn Tyr Thr Val Lys Phe Gln Gly
        115                 120                 125

Val Asn Phe Pro Leu Asp Gly Pro Val Met Gln Lys Lys Thr Arg Gly
    130                 135                 140

Trp Asp Pro Ser Thr Glu Arg Leu Tyr Glu Cys Asp Gly Trp Leu Arg
145                 150                 155                 160

Gly Asp Val Asp Met Ala Leu Lys Leu Glu Asn Gly Gly His Tyr Thr
                165                 170                 175

Cys Asn Phe Lys Thr Thr Tyr Lys Ser Lys Gly Leu Lys Val Pro
            180                 185                 190

Pro Tyr His Phe Val Asp His Lys Leu Asp Leu Leu Ser His Asn Thr
        195                 200                 205

Asp Gly Ala Thr Phe Glu Glu Phe Glu Gln Gln Glu Ile Ala His Ala
    210                 215                 220

His Leu Ser Lys Leu Ala
225                 230
```

<210> SEQ ID NO 2
<211> LENGTH: 230
<212> TYPE: PRT
<213> ORGANISM: Artificial Sequence
<220> FEATURE:
<223> OTHER INFORMATION: Mutant polypeptide having fluorescent property

<400> SEQUENCE: 2

Met Glu Ala Leu Ser Lys Gln Thr Gly Ile Gln Thr Glu Met Lys Thr
1               5                   10                  15

Lys Phe His Met Asp Gly Ile Val Asn Gly His Leu Phe Glu Ile Glu
            20                  25                  30

Gly Glu Gly Lys Gly Lys Pro Tyr Glu Gly Val Gln Thr Met Lys Leu
        35                  40                  45

Lys Val Thr Lys Gly Ala Pro Leu Pro Phe Ser Ile Asp Ile Leu Leu
    50                  55                  60

Pro Gln Val Met Tyr Gly Ser Lys Pro Phe Ile Lys Tyr Pro Glu Asn
65                  70                  75                  80

Ile Pro Asp Tyr Ile Lys Leu Ser Phe Pro Glu Gly Ile Thr Trp Glu
                85                  90                  95

Arg Thr Met Thr Phe Glu Asp Gly Ala Val Cys Thr Ala Ser Asn Asp
            100                 105                 110

Ser Ser Leu Glu Gly Asn Cys Phe Asn Tyr Lys Val Lys Phe Gln Gly
        115                 120                 125

Val Asn Phe Pro Gln Asp Gly Pro Ile Met Gln Lys Arg Thr Arg Gly
    130                 135                 140

Trp Glu Pro Ser Thr Glu Arg Leu Tyr Glu Trp Asp Gly Trp Gln Arg
145                 150                 155                 160

Gly Asp Val His Met Ala Leu Lys Leu Glu Asn Gly Gly Asn Tyr Thr
                165                 170                 175

Cys Asn Phe Lys Thr Thr Tyr Lys Ser Lys Lys Gly Leu Arg Val Ser
            180                 185                 190

Pro Tyr His Phe Val Asp His Lys Leu Asp Val Leu Ser Arg Asn Thr
        195                 200                 205

Asp Gly Ala Thr Phe Glu Glu Phe Glu Leu Arg Glu Ile Ala His Ala
    210                 215                 220

His Leu Ser Lys Leu Ala
225                 230

<210> SEQ ID NO 3
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 3
atggaaaatg tgcgacgaaa gagtggcatc cagactgaaa tgaagaccaa gctacatatg      60
gacgggatgg tcaatggaca ctcctttgag ataaaggag aaggaaaagg aagcccttac     120
gagggtgtgc agaccatgaa acttaaagtg accaagggtg cgcctttgcc attttctatt    180
gacattttgc tgcctcaatg catgtatgga agcaagccat tattaagta tcctgagaat     240 atcccagact acatcaagct gtcgtttcct gagggaatca catgggaaag aaccatgacc    300
tttgaggatg gtgcagtgtg cgatgtgtct aacgactcca gactcgttgg caactgtttc    360
aactacacag tcaagtttca aggtgtgaac tttcccctag atggacctgt tatgcagaag    420

```
aagacacgag gctgggaccc gtccactgag agactgtatg agtgtgatgg gtggctgagg      480
ggagatgtcg acatggcctt gaagttggag aacggtggcc attatacgtg caacttcaaa      540
actacttaca aatcgaagaa gggcttgaag gtgccaccgt atcacttcgt tgaccacaaa      600
ttagatctac tgagccacaa tactgatggc gctacctttg aagagtttga gcaacaagaa      660
attgctcatg cacatctttc taagttagcc taa                                   693
```

```
<210> SEQ ID NO 4
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 4
```

```
atggaagctc tttcaaagca aactgggatc caaactgaaa tgaagaccaa gtttcatatg      60
gacgggatcg tcaatggaca cctctttgag atagaaggag aaggaaaagg aaagccttac      120
gagggtgtgc agaccatgaa gcttaaagtc actaagggtg cgccttttgcc attttctatt      180 gcatttttgt tgcctcaagt aatgtatgga agcaagccat ttattaagta tcctgagaat      240
atcccagact acatcaagtt gtcatttccc gagggaatca catgggaaag aaccatgacc      300
ttcgaagatg gtgcagtgtg cactgcgtct aacgactcca gtctcgaggg caactgtttc      360
aactacaaag tcaagtttca aggtgtgaac tttccccaag atggacctat tatgcagaag      420
aggacacgag gctgggagcc atccactgag agactgtatg agtgggatgg gtggcagaga      480
ggagatgtcc acatggcctt gaagttggag aacggtggca attatacttg caacttcaaa      540
actacttaca atcaaaaaaa gggcttgagg gtgtcaccgt atcacttcgt tgaccacaaa      600
ctagatgtac tgagccgcaa caccgatggt gctacctttg aggagtttga gctgcgagaa      660
attgctcacg cacatctttc taagttagcc taa                                   693
```

```
<210> SEQ ID NO 5
<211> LENGTH: 230
<212> TYPE: PRT
<213> ORGANISM: Artificial Sequence
<220> FEATURE:
<223> OTHER INFORMATION: Mutant polypeptide having  fluorescent property

<400> SEQUENCE: 5
```

```
Met Glu Asn Val Arg Arg Lys Ser Gly Ile Gln Thr Glu Met Lys Thr
1               5                   10                  15

Lys Leu His Met Asp Gly Met Val Asn Gly His Ser Phe Glu Ile Lys
            20                  25                  30

Gly Glu Gly Lys Gly Ser Pro Tyr Glu Gly Val Gln Thr Met Lys Leu
        35                  40                  45

Lys Val Thr Lys Gly Ala Pro Leu Pro Phe Ser Ile Asp Ile Leu Leu
    50                  55                  60

Pro Gln His Met Tyr Gly Ser Lys Pro Phe Ile Lys Tyr Pro Glu Asn
65                  70                  75                  80

Ile Pro Asp Tyr Ile Lys Leu Ser Phe Pro Glu Gly Ile Thr Trp Glu
                85                  90                  95

Arg Thr Met Thr Phe Glu Asp Gly Ala Val Cys Thr Ala Ser Asn Asp
            100                 105                 110

Ser Arg Leu Val Gly Asn Cys Phe Asn Tyr Thr Val Lys Phe Gln Gly
        115                 120                 125
```

-continued

```
Val Asn Phe Pro Leu Asp Gly Pro Val Met Gln Lys Lys Thr Arg Gly
        130                 135                 140

Trp Asp Pro Ser Thr Glu Arg Leu Tyr Glu Cys Asp Gly Trp Leu Arg
145                 150                 155                 160

Gly Asp Val Asp Met Ala Leu Lys Leu Glu Asn Gly Gly His Tyr Thr
                165                 170                 175

Cys Asn Phe Lys Thr Thr Tyr Lys Ser Lys Lys Gly Leu Lys Val Pro
                180                 185                 190

Pro Tyr His Phe Val Asp His Lys Leu Asp Leu Leu Ser His Asn Thr
                195                 200                 205

Asp Gly Ala Thr Phe Glu Glu Phe Glu Gln Gln Glu Ile Ala His Ala
        210                 215                 220

His Leu Ser Lys Leu Ala
225                 230

<210> SEQ ID NO 6
<211> LENGTH: 230
<212> TYPE: PRT
<213> ORGANISM: Artificial Sequence
<220> FEATURE:
<223> OTHER INFORMATION: Mutant polypeptide having  fluorescent property

<400> SEQUENCE: 6

Met Glu Asn Val Arg Arg Lys Ser Gly Ile Gln Thr Glu Met Lys Thr
1               5                   10                  15

Lys Leu His Met Asp Gly Lys Val Asn Gly His Ser Phe Glu Ile Lys
                20                  25                  30

Gly Glu Gly Lys Gly Ser Pro Tyr Glu Gly Val Gln Thr Met Lys Leu
            35                  40                  45

Lys Val Thr Lys Gly Ala Pro Leu Pro Phe Ser Ile Asp Ile Leu Leu
        50                  55                  60

Pro Gln His Met Tyr Gly Ser Lys Pro Phe Ile Lys Tyr Pro Glu Asn
65                  70                  75                  80

Ile Pro Asp Tyr Ile Lys Leu Ser Phe Pro Glu Gly Ile Thr Trp Glu
                85                  90                  95

Arg Thr Met Thr Phe Glu Asp Gly Ala Val Cys Thr Ala Ser Asn Asp
                100                 105                 110

Ser Arg Leu Val Gly Asn Cys Phe Asn Tyr Thr Val Lys Phe Glu Gly
            115                 120                 125

Val Asn Phe Pro Leu Asp Gly Pro Val Met Gln Lys Lys Thr Arg Gly
        130                 135                 140

Trp Asp Pro Ser Thr Glu Arg Leu Tyr Glu Cys Asp Gly Trp Leu Arg
145                 150                 155                 160

Gly Asp Val His Met Ala Leu Lys Leu Glu Asn Gly Gly His Tyr Thr
                165                 170                 175

Cys Asn Phe Lys Thr Thr Tyr Lys Ser Lys Lys Gly Leu Lys Val Pro
                180                 185                 190

Pro Tyr His Phe Val Asp His Lys Leu Asp Leu Leu Ser His Asn Thr
                195                 200                 205

Asp Gly Ala Thr Phe Glu Glu Phe Glu Gln Gln Glu Ile Ala His Ala
        210                 215                 220

His Leu Ser Lys Leu Ala
225                 230

<210> SEQ ID NO 7
<211> LENGTH: 230
```

<212> TYPE: PRT
<213> ORGANISM: Artificial Sequence
<220> FEATURE:
<223> OTHER INFORMATION: Mutant polypeptide having fluorescent property

<400> SEQUENCE: 7

Met Glu Ala Leu Ser Lys Gln Thr Gly Ile Gln Thr Glu Met Lys Thr
1               5                   10                  15
Lys Phe His Met Asp Gly Ile Val Asn Gly His Leu Phe Glu Ile Glu
            20                  25                  30
Gly Glu Gly Lys Gly Lys Pro Tyr Glu Gly Val Gln Thr Met Lys Leu
        35                  40                  45
Lys Val Thr Lys Gly Ala Pro Leu Pro Phe Ser Ile Asp Ile Leu Leu
    50                  55                  60
Pro Gln Glu Met Tyr Gly Ser Lys Pro Phe Ile Lys Tyr Pro Glu Asp
65                  70                  75                  80
Ile Pro Asp Tyr Ile Lys Leu Ser Phe Pro Glu Gly Ile Thr Trp Glu
                85                  90                  95
Arg Thr Met Thr Phe Glu Asp Gly Ala Val Cys Thr Val Ser Asn Asp
            100                 105                 110
Ser Ser Leu Glu Gly Asn Cys Phe Ile Tyr Lys Val Lys Phe Gln Gly
        115                 120                 125
Val Asn Phe Pro Gln Asp Gly Pro Ile Met Gln Lys Lys Thr Arg Gly
    130                 135                 140
Trp Glu Pro Phe Thr Glu Arg Leu Tyr Glu Trp Asp Gly Trp Gln Arg
145                 150                 155                 160
Gly Asp Val His Met Ala Leu Lys Leu Glu Asp Gly Asn Tyr Thr
                165                 170                 175
Cys Asn Ser Lys Thr Thr Tyr Lys Ser Lys Lys Gly Leu Arg Val Pro
            180                 185                 190
Pro Tyr His Phe Val Asp His Lys Leu Asp Val Leu Ser His Asn Thr
        195                 200                 205
Asp Gly Val Thr Phe Glu Glu Phe Glu Gln Arg Glu Ile Ala His Ala
    210                 215                 220
His Leu Ser Lys Leu Ala
225                 230

<210> SEQ ID NO 8
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 8
atggaaaatg tgcgacgaaa gagtggcatc cagactgaaa tgaagaccaa gctacatatg      60
gacgggatgg tcaatggaca ctccttcgag ataaaggag aaggaaaagg aagcccttac      120
gagggtgtgc agaccatgaa acttaaagtg accaagggtg cgcctttgcc atttctatt      180 gacattttgc tgcctcaaca catgtatgga agcaagccat ttattaagta tcctgagaat      240
atcccagact acatcaagct gtcgtttcct gagggaatca catgggaaag aaccatgacc      300
tttgaggatg gtgcagtgtg cactgcctct aacgactcca gactcgttgg caactgtttc      360
aactacacag tcaagtttca aggtgtgaac tttcccctag atggacctgt tatgcagaag      420
aagacacgag gctgggaccc gtccactgag agactgtatg agtgtgatgg gtggctgagg      480

```
ggagatgtcg acatggcctt gaagttggag aacggtggcc attatacgtg caacttcaaa    540
actacttaca aatcgaagaa gggcttgaag gtgccaccgt atcacttcgt tgaccacaaa    600
ttagatctac tgagccacaa tactgatggc gctacctttg aagagtttga gcaacaagaa    660
attgctcatg cacatctttc taagttagcc taa                                 693

<210> SEQ ID NO 9
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 9
atggaaaatg tgcgacgaaa gagtggcatc cagactgaaa tgaagaccaa gctacatatg     60
gacgggaagg tcaatggaca ctccttcgag ataaaggag aaggaaaagg aagcccttac     120
gagggtgtgc agaccatgaa acttaaagtg accaagggtg cgcctttgcc attttctatt    180
gacattttgc tgcctcaaca catgtatgga agcaagccat ttattaagta tcctgagaat    240
atcccagact acatcaagct gtcgtttcct gagggaatca catgggaaag aaccatgacc    300
tttgaggatg gtgcagtgtg cactgcctct aacgactcca gactcgttgg caactgtttc    360
aactacacag tcaagtttga aggtgtgaac tttcccctag atggacctgt tatgcagaag    420
aagacacgag gctgggaccc gtccactgag agactgtatg agtgtgatgg gtggctgaga    480
ggagatgtcc acatggcctt gaagttggag aacggtggcc attatacgtg caacttcaaa    540
actacttaca aatcgaagaa gggcttgaag gtgccaccgt atcacttcgt tgaccacaaa    600
ttagatctac tgagccacaa tactgatggc gctacctttg aagagtttga gcaacaagaa    660
attgctcatg cacatctttc taagttagcc taa                                 693

<210> SEQ ID NO 10
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 10
atggaagctc tttcaaagca aactgggatc caaactgaaa tgaagactaa gtttcatatg     60
gacgggatcg tcaatggaca cctctttgag atagaaggag aaggaaaagg aaagccttac    120
gagggtgtgc agaccatgaa gcttaaagtc actaagggtg cgcctttgcc attttctatt    180
gacattttgc tgcctcaaga aatgtacgga agcaagccat ttattaagta tcctgaggat    240
atcccagact acatcaagtt gtcatttccc gagggaatca catgggaaag aaccatgacc    300
ttcgaagatg gtgcagtgtg cactgtgtct aacgactcca gtctcgaggg caactgtttc    360
atctacaaag tcaagtttca aggtgtgaac tttcccccaag atgggcctat tatgcagaag    420
aagacacgag gctgggagcc attcactgag agactgtatg agtgggatgg gtggcagaga    480
ggagatgtcc acatggcctt gaagttggag acggtggca attatacttg caactccaaa    540
actacttaca aatcaaaaaa gggcttgagg gtgccaccgt atcacttcgt tgaccacaaa    600
ctagatgtac tgagccacaa caccgatggt gttacctttg aagaatttga gcaacgagaa    660
attgctcacg cacatctttc taagttagcc taa                                 693
```

```
<210> SEQ ID NO 11
<211> LENGTH: 44
<212> TYPE: DNA
<213> ORGANISM: Artificial Sequence
<220> FEATURE:
<223> OTHER INFORMATION: Primer for reverse transcription

<400> SEQUENCE: 11
gactagttct agatcgcgag cggccgccct tttttttttt tttt            44

<210> SEQ ID NO 12
<211> LENGTH: 30
<212> TYPE: DNA
<213> ORGANISM: Artificial Sequence
<220> FEATURE:
<223> OTHER INFORMATION: forward primer

<400> SEQUENCE: 12
gacgcggtac catggaagct ctttcaaagc                            30

<210> SEQ ID NO 13
<211> LENGTH: 32
<212> TYPE: DNA
<213> ORGANISM: Artificial Sequence
<220> FEATURE:
<223> OTHER INFORMATION: reverse primer

<400> SEQUENCE: 13
aggaggaatt cttaggctaa cttagaaaga tg                         32

<210> SEQ ID NO 14
<211> LENGTH: 32
<212> TYPE: DNA
<213> ORGANISM: Artificial Sequence
<220> FEATURE:
<223> OTHER INFORMATION: forward primer

<400> SEQUENCE: 14
gacgcggtac catggaaaat gtgcgacgaa ag                         32

<210> SEQ ID NO 15
<211> LENGTH: 32
<212> TYPE: DNA
<213> ORGANISM: Artificial Sequence
<220> FEATURE:
<223> OTHER INFORMATION: reverse primer

<400> SEQUENCE: 15
aagatgaatt cttaggctaa cttagaaaga tg                         32

<210> SEQ ID NO 16
<211> LENGTH: 230
<212> TYPE: PRT
<213> ORGANISM: Artificial Sequence
<220> FEATURE:
<223> OTHER INFORMATION: Mutant polypeptide having  fluorescent property

<400> SEQUENCE: 16

Met Glu Asn Val Arg Arg Lys Thr Gly Ile Gln Thr Glu Met Lys Thr
1               5                   10                  15

Lys Leu His Met Asp Gly Met Val Asn Gly His Ser Phe Glu Ile Lys
                20                  25                  30

Gly Glu Gly Lys Gly Ser Pro Tyr Glu Gly Val Gln Thr Met Lys Leu
            35                  40                  45

Lys Val Thr Lys Gly Ala Pro Leu Pro Phe Ser Ile Asp Ile Leu Leu
```

```
                    50                  55                  60
Pro Gln Cys Met Tyr Gly Ser Lys Pro Phe Ile Lys Tyr Pro Glu Asn
 65                  70                  75                  80

Ile Pro Asp Tyr Ile Lys Leu Ser Phe Pro Glu Gly Ile Thr Trp Glu
                 85                  90                  95

Arg Thr Met Thr Phe Glu Asp Gly Ala Val Cys Asp Val Ser Asn Asp
            100                 105                 110

Ser Arg Leu Val Gly Asn Cys Phe Ile Tyr Thr Val Lys Phe Gln Gly
        115                 120                 125

Val Asn Phe Pro Leu Asp Gly Pro Val Met Gln Lys Lys Thr Arg Gly
    130                 135                 140

Trp Glu Pro Ser Thr Glu Val Leu Tyr Glu Cys Asp Gly Trp Met Arg
145                 150                 155                 160

Gly Leu Val Asp Ile Ala Leu Lys Leu Glu Asn Gly Gly His Tyr Thr
                165                 170                 175

Cys Asn Phe Lys Thr Thr Tyr Lys Ser Lys Lys Gly Leu Glu Val Pro
            180                 185                 190

Pro Tyr His Phe Val Asp His Lys Leu Asp Leu Leu Ser His Asn Thr
        195                 200                 205

Asp Gly Ala Thr Phe Glu Glu Phe Glu Gln Gly Glu Ile Ala His Ala
    210                 215                 220

His Leu Ser Lys Leu Ala
225                 230

<210> SEQ ID NO 17
<211> LENGTH: 693
<212> TYPE: DNA
<213> ORGANISM: Artificial Sequence
<220> FEATURE:
<223> OTHER INFORMATION: Mutant gene coding for polypeptide having
      fluorescent property

<400> SEQUENCE: 17
atggagaacg tcaggagaaa gacaggcatt cagacggaaa tgaaaacgaa gctccacatg      60
gatggtatgg tgaatggaca cagctttgag atcaaagggg aggggaaggg aagcccgtac     120 gaggggggtgc agacaatgaa gctgaaggtt actaagggcg ccccacttcc cttctctata    180
gacattcttt tgcctcagtg catgtatggc agcaaacctt tcattaaata tcctgagaac     240
atccccgatt atattaaact ctcatttcca gagggtatca cttgggagag acaatgaca      300 ttcgaggacg gcgcagtatg cgatgtatct aatgattcca gactggtcgg caattgcttt     360
atctacactg tgaagtttca gggagtcaat tttccacttg atggccccgt tatgcaaaag     420
aagacccgag ctgggaacc ctccactgaa gtgctgtacg aatgtgatgg gtggatgcgc      480
gggttggtgg acatagctct gaaactggaa aacggtggac attatacatg taatttcaag    540
accacctaca atccaagaa aggtcttgag gtgccacctt accatttcgt ggatcataaa      600
ctcgacctgc tcagtcataa caccgacgga gccacctttg aggagttcga acaaggtgaa    660
atcgctcacg cgcacttgag taaactggcc tga                                 693

<210> SEQ ID NO 18
<211> LENGTH: 230
<212> TYPE: PRT
<213> ORGANISM: Artificial Sequence
<220> FEATURE:
<223> OTHER INFORMATION: Mutant polypeptide having  fluorescent property

<400> SEQUENCE: 18
```

```
Met Glu Asn Val Arg Arg Lys Thr Gly Ile Gln Thr Glu Met Lys Thr
1               5                   10                  15

Lys Leu His Met Asp Gly Met Val Asn Gly His Ser Phe Glu Ile Lys
            20                  25                  30

Gly Glu Gly Lys Gly Ser Pro Tyr Glu Gly Val Gln Thr Met Lys Leu
        35                  40                  45

Lys Val Thr Lys Gly Ala Pro Leu Pro Phe Ser Ile Asp Ile Leu Leu
    50                  55                  60

Pro Gln Cys Met Tyr Gly Ser Lys Pro Phe Ile Lys Tyr Pro Glu Asn
65              70                  75                  80

Ile Pro Asp Tyr Leu Lys Leu Ser Phe Pro Glu Gly Ile Thr Trp Glu
                85                  90                  95

Arg Thr Met Thr Phe Glu Asp Gly Ala Val Cys Asp Val Ser Asn Asp
            100                 105                 110

Ser Arg Leu Val Gly Asn Cys Phe Ile Tyr Thr Val Lys Phe Gln Gly
        115                 120                 125

Val Asn Phe Pro Leu Asp Gly Pro Val Met Gln Lys Lys Thr Arg Gly
    130                 135                 140

Trp Glu Pro Ser Thr Glu Val Leu Tyr Glu Cys Asp Gly Trp Met Arg
145             150                 155                 160

Gly Leu Val Asp Ile Ala Leu Lys Leu Glu Asn Gly Gly His Tyr Met
                165                 170                 175

Cys Asn Phe Lys Thr Thr Tyr Lys Ser Lys Lys Gly Leu Glu Val Pro
            180                 185                 190

Pro Tyr His Phe Val Asp His Lys Leu Asp Leu Leu Ser His Asn Thr
        195                 200                 205

Asp Gly Ala Thr Phe Glu Glu Phe Glu Gln Gly Glu Ile Ala His Ala
    210                 215                 220

His Leu Ser Lys Leu Ala
225             230
```

<210> SEQ ID NO 19
<211> LENGTH: 693
<212> TYPE: DNA
<213> ORGANISM: Artificial
<220> FEATURE:
<223> OTHER INFORMATION: Mutant gene coding for polypeptide having
      fluorescent property

<400> SEQUENCE: 19

```
atggagaacg tcaggagaaa gacaggcatt cagacggaaa tgaaaacgaa gctccacatg      60
gatggtatgg tgaatggaca cagctttgag atcaaagggg aggggaaggg aagcccgtac     120
gagggggtgc agacaatgaa gctgaaggtt actaagggcg cccacttcc cttctctata      180 gacattcttt tgcctcagtg catgtatggc agcaaacctt tcattaaata tcctgagaac     240
atccccgatt atttgaaact ctcatttcca gagggtatca cttgggagag gacaatgaca     300
ttcgaggacg gcgcagtatg cgatgtatct aatgattcca gactggtcgg caattgcttt     360
atctacactg tgaagtttca gggagtcaat tttccacttg atggccccgt tatgcaaaag     420
aagacccgag ctgggaaacc ctccactgaa gtgctgtacg aatgtgatgg gtggatgcgc     480
gggttggtgg acatagctct gaaactggaa aacggtggac attatatgtg taattttaag     540
accacctaca atccaagaa aggtcttgag gtgccacctt accatttcgt ggatcataaa      600
```

```
ctcgacctgc tcagtcataa caccgacgga gccacctttg aggagttcga acaaggtgaa     660
atcgctcacg cgcacttgag taaactggcc tga                                 693
```

POLYPEPTIDE EXHIBITING FLUORESCENT PROPERTIES, AND UTILIZATION OF THE SAME

CROSS REFERENCE TO RELATED APPLICATIONS

This application is a U.S. National Stage Application of PCT/JP2014/072039 filed on Aug. 22, 2014, which claims priority to Japanese patent application 2013-173850 filed on Aug. 23, 2013, the contents of both of which are incorporated herein by reference.

TECHNICAL FIELD

The present invention relates to a polypeptide exhibiting a fluorescence property, and utilization of the same.

BACKGROUND ART

Fluorescent proteins are an indispensable tool for visualizing a cell, tissue, individual organism, or the like. Patent Literature 1, for example, discloses a fluorescent protein that emits green fluorescence. Further, various protein mutants have been reported for fluorescent proteins emitting red fluorescence as well (Patent Literature 2, Non Patent Literatures 1-3).

CITATION LIST

Patent Literature

Patent Literature 1
U.S. Pat. No. 5,491,084 (Feb. 13, 1996)
Patent Literature 2
U.S. Pat. No. 7,166,444 (Jan. 23, 2007)

Non Patent Literature

Non Patent Literature 1
Shaner N C, Campbell R E, Steinbach P A, Giepmans B N, Palmer A E, Tsien R Y. Nature Biotechnolgy. 2004; 22 (12): p1567-72. Epub 2004 Nov. 21.
Non Patent Literature 2
S Ekaterina M Merzlyak, Joachim Goedhart, Dmitry Shcherbo, Mariya E Bulina, Aleksandr S Shcheglov, Arkady F Fradkov, Anna Gaintzeva, Konstantin A Lukyanov, Sergey Lukyanov, Theodorus W J Gadella & Dmitriy M Chudakov. Nature Methods. 2007; 4, p555-557
Non Patent Literature 3
Simone Kredel, Franz Oswald, Karin Nienhaus, Karen Deuschle, Carlheinz Rocker, Michael Wolff, Ralf Heilker, G. Ulrich Nienhaus, and Jorg Wiedenmann. PLoS ONE. 2009; 4 (2): e4391.

SUMMARY OF INVENTION

Technical Problem

In recent years, there has been an increasing demand for labeling a cell or protein with use of a fluorescent protein. As the demand grows, properties required for a fluorescent protein have been diversified. Thus, a novel fluorescent protein different from conventional fluorescent proteins has been needed.

It is an object of the present invention to provide a fluorescent protein that is a mutant of a fluorescent protein derived from *Montipora monasteriata* and that exhibits a useful characteristic as a fluorescent protein.

Solution to Problem

In order to solve the above problem, the present invention includes in its scope any one mode below.

<1> A polypeptide having a fluorescence property, the polypeptide being defined in any one of (1) to (4) below: (1) A polypeptide having an amino acid sequence represented by SEQ ID NO. 1 or NO. 2, (2) A polypeptide having an amino acid sequence represented by SEQ ID NO. 1 or NO. 2 in which amino acid sequence 1 to 34 amino acids have been replaced, deleted, inserted, and/or added, (3) A polypeptide having a sequence identity of 85% or more with respect to the amino acid sequence represented by SEQ ID NO. 1 or NO. 2, and (4) A polypeptide encoded by a polynucleotide that hybridizes under a stringent condition with a polynucleotide having a sequence complementary to a polynucleotide that encodes the polypeptide defined in (1) above.

<2> A polynucleotide defined in any one of (1) to (4) below: (1) A polynucleotide encoding a polypeptide having an amino acid sequence represented by SEQ ID NO. 1 or NO. 2, (2) A polynucleotide encoding a polypeptide that has an amino acid sequence represented by SEQ ID NO. 1 or NO. 2 in which amino acid sequence 1 to 34 amino acids have been replaced, deleted, inserted, and/or added and that has a fluorescence property, (3) A polynucleotide encoding a polypeptide that has a sequence identity of 85% or more with respect to the amino acid sequence represented by SEQ ID NO. 1 or NO. 2 and that has a fluorescence property, and (4) A polynucleotide encoding a polypeptide that hybridizes under a stringent condition with a polynucleotide having a sequence complementary to the polynucleotide defined in (1) above and that has a fluorescence property.

<3> An expression cassette including: (a) an expression regulatory region functional in an expression host; and (b) a polynucleotide according to <2>.

<4> A vector including: a polynucleotide according to <2>; or an expression cassette according to <3>.

<5> A transformant including: a polynucleotide according to <2>; an expression cassette according to <3>; or a vector according to <4>.

<6> A fusion polypeptide including: a polypeptide according to <1>; and another polypeptide.

<7> A method for fluorescence observation, the method including the steps of: producing, in a cell, a polypeptide according to <1> or a fusion polypeptide according to <6>; and observing fluorescence from the polypeptide or the fusion polypeptide.

<8> A method for evaluating effect of one or more test substances on expression and/or localization of one or more target genes in a cell, the method including the steps of: (i) introducing, into cells, a first nucleic acid molecule including a polynucleotide according to <2> which polynucleotide may be fused with a first target gene, the first nucleic acid molecule being operably linked to a first expression regulatory sequence so as to be under control of the first expression regulatory sequence; (ii) culturing the cells, resulting from the step (i), in presence of and in absence of the one or more test substances; (iii) detecting respective fluorescence emissions in the cells; and (iv) comparing the respective fluorescence emissions in the cells, produced in the presence of and in the absence of the one or more test substances, so as to evaluate the effect of the one or more test substances on the expression and/or localization of the one or more target genes.

<9> A method for producing a transformant including, in a cell, all or part of a polynucleotide according to <2>, the method including the step of introducing, into a cell, a polynucleotide according to <2>, an expression cassette according to <3>, or a vector according to <4>.

<10> A transformant produced by a method according to <9> or progeny of the transformant.

<11> A method for producing a non-human transgenic organism including, in a cell, all or part of a polynucleotide according to <2>, the method including the step of introducing, into a fertilized egg collected from a donor cell, a polynucleotide according to <2>, an expression cassette according to <3>, or a vector according to <4>.

<12> A non-human transgenic organism produced by a method according to <11> or progeny of the non-human transgenic organism.

<13> A method for establishing a pluripotent stem cell, the method including the steps of: collecting a cell from a non-human transgenic organism or progeny thereof according to <12>; and introducing a reprogramming factor into the cell.

<14> A kit including: a polypeptide according to <1>; a polynucleotide according to <2>; an expression cassette according to <3>; a vector according to <4>; a transformant according to <5>; or a fusion polypeptide according to <6>.

Advantageous Effects of Invention

The present invention provides a fluorescent polypeptide that has fluorescence stability and early fluorescence emission when introduced in a cell. The fluorescent polypeptide of the present invention is advantageously useful in many biological fields such as molecular biology.

BRIEF DESCRIPTION OF DRAWINGS

FIG. 17 provides images that show local expression of mAzalea_B5, which is a protein according to still another Example of the present invention, in the endoplasmic reticulum of a HeLa cell.

DESCRIPTION OF EMBODIMENTS

Figure 1:
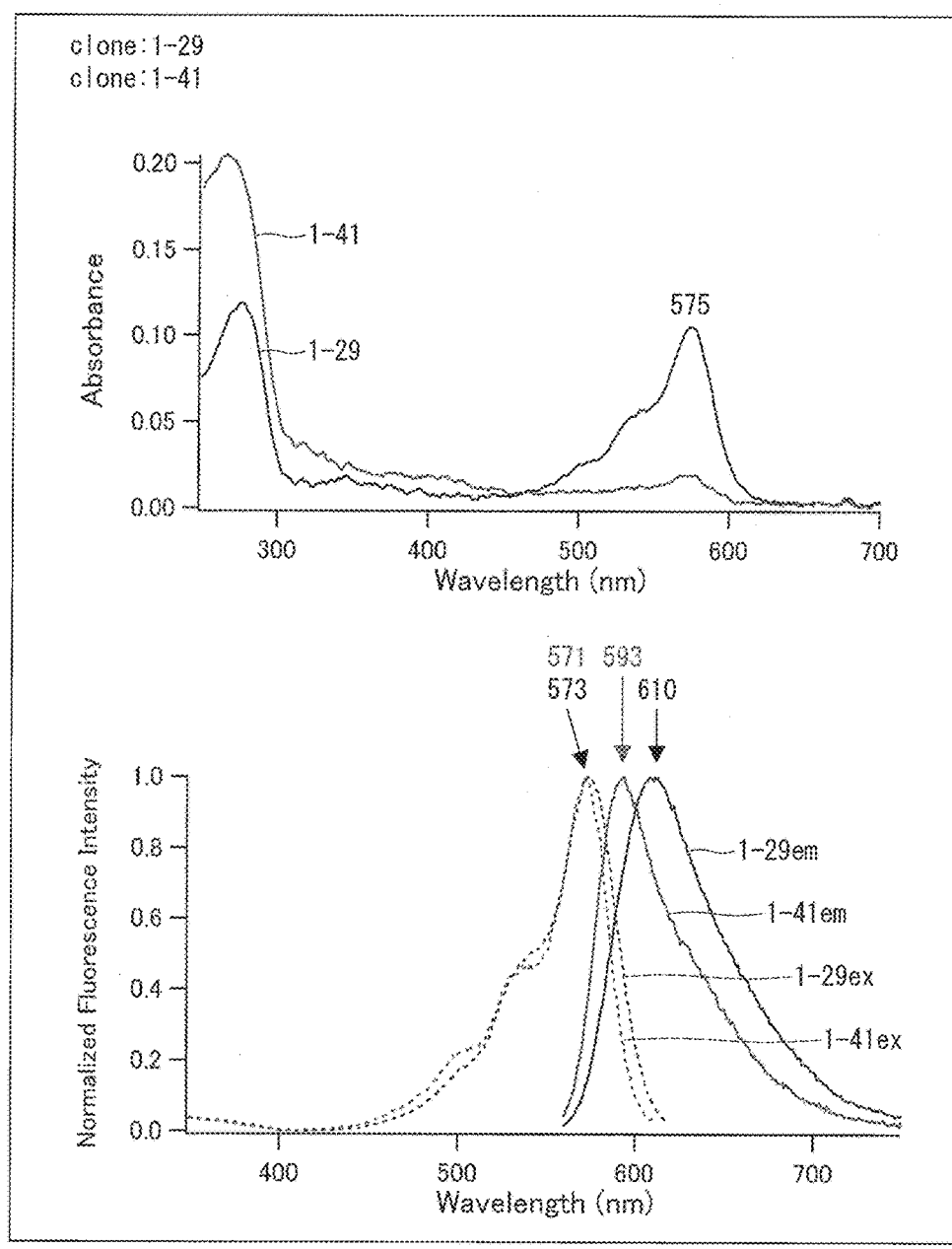
FIG. 1 provides graphs that show the respective fluorescence properties of proteins 1-29 and 1-41 in an Example of the present invention.

The description below deals with an embodiment of the present invention in detail.

Definitions of Terms and the Like

In the present specification, the term "polynucleotide" is interchangeable with "nucleic acid" or "nucleic acid molecule". The term "polynucleotide", unless otherwise specified, includes in its scope a polynucleotide that contains an already known analog of a natural form nucleotide having a function as well as the natural form nucleotide. The term "base sequence" is interchangeable with "nucleic acid sequence" or "nucleotide sequence", and intends to refer to a deoxyribonucleotide sequence or a ribonucleotide sequence unless otherwise indicated. The polynucleotide may have a single-stranded structure or a double-stranded structure, and may be a sense strand or an antisense strand in the case of a single strand.

In the present specification, the term "gene" refers to a "polynucleotide" that encodes a protein.

In the present specification, an "expression regulatory region" of a gene refers to a "polynucleotide" that regulates expression of the gene. Examples of the "expression regulatory region" include a promoter region and an enhancer region.

In the present specification, the term "expression cassette" refers to an expression unit including (i) a functional expression regulatory region in a host to be expressed and (ii) a polynucleotide operably linked to the expression regulatory region. In the expression cassette, the polynucleotide is preferably a gene or a gene fragment. An example of the expression cassette is a polynucleotide linked the above expression regulatory region to the above polynucleotide in a genetically engineered manner. The term "operably linked" refers to a state in which expression of a polynucleotide is controlled with use of an expression regulatory sequence. The expression cassette may be in the form of an expression vector.

In the present specification, the term "polypeptide" is interchangeable with "protein". A "polypeptide" includes a structure of amino acids linked by a peptide bond. A "polypeptide" may further include a structure of a sugar chain or an isoprenoid group and the like. The term "polypeptide", unless otherwise specified, includes in its scope a polypeptide that contains an already known analog of a natural form amino acid having a function as well as the natural form amino acid.

In the present specification, the term "fluorescent polypeptide" refers to a polypeptide having a fluorescence property. A polypeptide having a fluorescence property is a polypeptide that emits fluorescence in response to irradiation of excitation light having a certain wavelength.

In the present specification, the expression "A and/or B" is a concept covering both "A and B" and "A or B", and is interchangeable with "at least one of A and B".

[1. Polypeptide Having Fluorescence Property]

(1-1: Fluorescent Polypeptide A)

A polypeptide A according to the present invention is a fluorescent polypeptide defined in any one of (1) to (4) below:

(1) A fluorescent polypeptide having an amino acid sequence represented by SEQ ID NO. 1 or NO. 2.

(2) A fluorescent polypeptide having an amino acid sequence represented by SEQ ID NO. 1 or NO. 2 in which amino acid sequence 1 to 34 amino acids have been replaced, deleted, inserted, and/or added. The number of amino acids that have been replaced, deleted, inserted, and/or added is preferably 1 to 25, more preferably 1 to 23, even more preferably 1 to 12, particularly preferably 1 to 5 or 1 to 6. The description below may use amino acid mutation as a collective term for replacement, deletion, insertion, and/or addition of amino acids.

(3) A fluorescent polypeptide having a sequence identity of 85% or more with respect to the amino acid sequence represented by SEQ ID NO. 1 or NO. 2. The sequence identity is preferably 88% or more, more preferably 90% or more, even more preferably 95% or more, particularly preferably 96% or more, 97% or more, 98% or more, or 99% or more.

(4) A fluorescent polypeptide encoded by a polynucleotide that hybridizes under a stringent condition with a polynucleotide having a sequence complementary to a polynucleotide that encodes the fluorescent polypeptide defined in (1) above. The stringent condition will be described in a later section of a polynucleotide according to the present invention.

The examples of process of the fluorescent polypeptide A are, not limited to, chemical synthesis or production by gene recombination technique. More specifically, the fluorescent polypeptide A includes in its scope an isolated and purified polypeptide, a chemically synthesized polypeptide, and a polypeptide produced from a host cell on the basis of a gene recombination technique. The host cell will be described in detail in a later section of "transformant".

An example of the fluorescent polypeptide A is a fluorescent polypeptide of which the amino acid sequence is represented by SEQ ID NO. 1 or NO. 2.

The fluorescent polypeptides A defined in (2) to (4) above can each be regarded as a mutant in a case where the fluorescent polypeptide A defined in (1) is the standard form. The fluorescent polypeptides defined in (2) to (4) may be obtained by expressing a mutant which is artificially introduced a mutation into the polynucleotide encoding a fluorescent polypeptide defined in (1) by site-directed mutagenesis. Examples of the site-specific mutagenesis include a Kunkel method (Kunkel et al. (1985): Proc. Natl. Acad. Sci. USA, vol. 82, p. 488-). The fluorescent polypeptides A defined in (2) to (4) above are, for example, fluorescent polypeptides having amino acid sequences represented by SEQ IDs NO. 5 to NO. 7.

In a fluorescent polypeptide, X—Y-G (where X is any amino acid) is known as an amino acid sequence that forms a chromophore. In the fluorescent polypeptide A defined in (1) above, the sequence of amino acids 68 to 70 in each of SEQ IDs NO. 1 and NO. 2 is M-Y-G. Thus, in the fluorescent polypeptides A defined in (2) to (4) above, amino acid 68 in each of SEQ IDs NO. 1 and NO. 2 may be replaced. It is, however, preferable to maintain amino acids 69 and 70 without mutation, and more preferable to maintain all of amino acids 68 to 70 without mutation.

The region other than the region of amino acids 69 and 70 in each of SEQ IDs NO. 1 and NO. 2 is, on the other hand, suitable for introducing amino acid mutation. Among other regions in each of SEQ IDs NO. 1 and NO. 2, regions such as respective regions of amino acids 3 to 8, 65 to 67 (preferably 67), 71 to 73 (preferably 72), 77 to 82, 104 to 112 (preferably 106 to 110, more preferably 108), 119 to 129, 131 to 135, 139 to 143, 146 to 150 (preferably 146 to 148, more preferably 146 or 148), 158 to 172 (preferably 159 to 166, more preferably 162 to 166, even more preferably 164), 177 to 181 (preferably 179), 190 to 194, 196 to 202 (preferably 199), 204 to 212, and 216 to 220 are more suitable for introducing amino acid mutation. In addition to the above regions specified as examples, any region in which corresponding amino acids differ from each other between SEQ IDs NO. 1 and NO. 2 is more suitable for introducing amino acid mutation. For example, sequence information of mAzalea or mAzalea_B5 in the Examples described later suggests that other than the positions specified above, amino acids 85, 151, and 176 of each of SEQ IDs NO. 1 and NO. 2 may each be replaced with another amino acid.

The fluorescent polypeptides A defined in (2) to (4) above may each exhibit a fluorescence property equivalent to that of the fluorescent polypeptide A having the amino acid sequence represented by SEQ ID NO. 1 or NO. 2. The term "fluorescence property equivalent to" means that the fluorescent polypeptide A has at least one property, among excitation wavelength, fluorescence wavelength, pH sensitivity, fluorescence stability, molar extinction coefficient, fluorescence quantum efficiency, excitation spectrum shape or emission spectrum shape, excitation wavelength maximum or emission wavelength maximum, excitation amplitude ratio between two different wavelengths, emission amplitude ratio between two different wavelengths, excited-state lifetime, and chromophore maturation rate, equivalent to that of the fluorescent polypeptide A having the amino acid sequence represented by SEQ ID NO. 1 or NO. 2. The term "fluorescence property equivalent to" preferably means that the fluorescent polypeptide A has equivalent fluorescence stability and fluorescence emission earliness when introduced in a cell and equivalent quantum yield. Specifically, the fluorescence stability of a fluorescent polypeptide A introduced in a cell means that the fluorescent polypeptide A does not form an aggregate in the cell and that the quantum yield Φ is 0.4 or more, preferably 0.6 or more. The expression "fluorescence property equivalent to" more preferably means that the fluorescent polypeptide A has not only equivalent quantum yield but also equivalent excitation wavelength, specifically, an excitation wavelength of 550 nm to 600 nm.

The fluorescent polypeptides A may be a monomer or a multimer. The fluorescent polypeptide is preferably a monomer in a case where, for example, the fluorescent polypeptide is used to label a molecule or used as a FRET (fluorescence resonance energy transfer) probe. In the amino acid sequence represented by SEQ ID NO. 1, respective regions of amino acids 104 to 112 (preferably 106 to 110, more preferably 108), 119 to 129, 131 to 135, 139 to 143, 146 to 150, and 158 to 172 (preferably 162 to 166, more preferably 164) are all presumed to be involved particularly in formation of a fluorescent polypeptide A multimer.

In the amino acid sequence represented by each of SEQ IDs NO. 1 and NO. 2, respective regions of amino acids 65 to 67 (preferably 67), 146 to 150 (preferably 148), 158 to 172 (preferably 159), 177 to 181 (preferably 179), and 196 to 202 (preferably 199) are all presumed to be involved particularly in shift of fluorescence wavelength. Thus, to produce a fluorescent polypeptide A with shifted fluorescence wavelength, it is preferable to cause mutation in at least one of the above amino acid regions. More preferably, the amino acid mutation is amino acid replacement.

An example fluorescent polypeptide A has a fluorescence quantum yield Φ of, for example, 0.6 (60%) or more, preferably 0.65 (65%) or more, more preferably 0.7 (70%) or more, at a pH 7.4. As demonstrated in the Examples, this value of quantum yield is significantly high as compared with conventional red fluorescent proteins. A larger fluorescence quantum yield allows a higher fluorescence intensity, with the result of a brighter fluorescence in general. A fluorescent polypeptide A with a large fluorescence quantum yield is more suitable for use in, for example, fluorescence observation. An example fluorescent polypeptide A having such a fluorescence quantum yield is a polypeptide A having a red fluorescence.

Another example fluorescent polypeptide A has a fluorescence quantum yield Φ of, for example, 0.40 (40%) or more, preferably 0.45 (45%) or more, more preferably 0.55 (55%) or more, at a pH 7.4. This example fluorescent polypeptide A has a molar extinction coefficient ($M^{-1}$ $cm^{-1}$) of, for example, 70000 or more, preferably 80000 or more, more preferably 100000 or more.

[2. Polynucleotide Encoding Fluorescent Polypeptide]

A polynucleotide according to the present invention encodes any one of the above fluorescent polypeptides A.

The polynucleotide encoding the fluorescent polypeptide A is specifically a polynucleotide defined in any one of (1-1) to (1-4) below.

(1-1) A polynucleotide encoding a polypeptide having the amino acid sequence represented by SEQ ID NO. 1 or NO. 2.

(1-2) A polynucleotide encoding a polypeptide that has an amino acid sequence represented by SEQ ID NO. 1 or NO. 2 in which amino acid sequence 1 to 34 amino acids have been replaced, deleted, inserted, and/or added and that has a fluorescence property. The number of amino acids that have been replaced, deleted, inserted, and/or added is preferably 1 to 25, more preferably 1 to 23, even more preferably 1 to 12, particularly preferably 1 to 5 or 1 to 6.

(1-3) A polynucleotide encoding a polypeptide that has a sequence identity of 85% or more with respect to the amino acid sequence represented by SEQ ID NO. 1 or NO. 2 and that has a fluorescence property. The sequence identity is preferably 88% or more, more preferably 90% or more, even more preferably 95% or more, particularly preferably 96% or more, 97% or more, 98% or more, or 99% or more.

(1-4) A polynucleotide encoding a polypeptide that hybridizes under a stringent condition with a polynucleotide having a sequence complementary to the polynucleotide defined in (1-1) above and that has a fluorescence property. The polynucleotide preferably has a sequence identity of 85% or more with respect to the base sequence of the polynucleotide defined in (1-1) above. The sequence identity is preferably 88% or more, more preferably 90% or more, even more preferably 95% or more, particularly preferably 96% or more, 97% or more, 98% or more, or 99% or more.

The stringent condition is, for example, a condition described in the reference document "Molecular cloning—a Laboratory manual 2nd edition" (Sambrook et al., 1989). A more specific example of the stringent condition is a hybridization condition of incubating the subject at 65° C. for 8 to 16 hours together with a probe in a solution containing 6×SSC (composition of 1×SSC: 0.15 M of sodium chloride, 0.015 M of citric acid sodium, pH 7.0), 0.5% SDS, 5×Denhardt, and 100 mg/mL of herring sperm DNA.

A polynucleotide according to the present invention may be present in the form of an RNA or a DNA. The form of an RNA is, for example, mRNA. The form of a DNA is, for example, cDNA or genomic DNA. The DNA may be double-stranded or single-stranded.

The respective base sequences represented by SEQ IDs NO. 3, NO. 4, and NO. 8 to NO. 10, each of which base sequences is an example polynucleotide according to the present invention, are cDNAs encoding the respective fluorescent polypeptides A represented by SEQ IDs NO. 1, NO. 2, and NO. 5 to NO. 7. The respective polypeptides having the base sequences represented by SEQ IDs NO. 17 to NO. 19, each of which polypeptides is another example polynucleotide according to the present invention, are cDNAs encoding the respective fluorescent polypeptides A represented by SEQ IDs NO. 16 and NO. 18. A polynucleotide according to the present invention may have an additional sequence such as a sequence of an untranslated region (UTR).

The method for producing (isolating) a polynucleotide according to the present invention is not particularly limited. A polynucleotide according to the present invention may be produced by, for example, (i) preparing a probe that hybridizes specifically with part of the base sequence of the polynucleotide and (ii) screening a genomic DNA library or a cDNA library. Alternatively, a polynucleotide according to the present invention may be synthesized by a nucleic acid synthesis method such as a phosphoramidite method.

A polynucleotide according to the present invention may be produced by, for example, a method that involves nucleic acid amplification such as PCR. An example method involves (i) preparing a primer from each of a 5' side and a 3' side of the sequence (or complementary sequences thereof) of cDNA of the polynucleotide, (ii) performing, for example, PCR by using the above primers with genomic DNA, cDNA, or the like as a template, and (iii) amplifying the DNA region between the two primers. This method allows a DNA fragment containing a polynucleotide according to the present invention to be produced in a large amount.

[3. Vector, Expression Cassette]

A polynucleotide according to the present invention (for example, DNA) may be inserted in an appropriate vector for use in the form of a vector. The vector may be of a kind such that the vector replicates itself autonomously as with a plasmid or that the vector is, when introduced into a host cell, integrated with a genome of the host cell and is replicated together with a chromosome of the host cell.

The above vector is preferably an expression vector. In the expression vector, a polynucleotide according to the present invention is functionally linked to, for example, elements necessary for transcription (such as a promoter sequence) that are functionally linked to each other. A promoter sequence is a DNA sequence that exhibits transcriptional activity in a host cell. The kind of the promoter sequence to be used may be selected as appropriate depending on the kind of the host cell and the purpose of using a fluorescent polypeptide according to the present invention. Example kinds of the host cell include those described under [4. Transformant and Method for Producing Transformant].

A promoter sequence operable in a host cell is, for example, a promoter of *Bacillus stearothermophilus* maltogenic amylase gene, *Bacillus licheniformis* alpha-amylase gene, *Bacillus amyloliquefaciens* BAN amylase gene, *Bacillus Subtilis* alkaline protease gene, or *Bacillus pumilus* xylosldase gene; a PR promoter or PL promoter of phage lambda; lac promoter, trp promoter, or tac promoter of *Escherichia coli*; or polyhedrin promoter, P10 promoter, *autographa californica* polyhedrosis basic protein promoter, baculovirus immediate-type early gene 1 promoter, baculovirus 39K delayed-type early gene promoter, a promoter derived from yeast glycolysis gene, alcohol dehydrogenase gene promoter, TPI1 promoter, ADH2-4c promoter, ADH3 promoter, tpiA promoter, 35S promoter of cauliflower mosaic virus, SV40 promoter, MT-1 (metallothionein gene) promoter, cytomegalo promoter, or adenovirus 2 major late promoter.

In an expression vector, a polynucleotide according to the present invention may be functionally bonded as necessary to an appropriate terminator (for example, polyadenylation signal, growth hormone terminator of a mammal, TPI1 terminator, or ADH3 terminator). The kind of the appropriate terminator may be selected as appropriate depending on the kind of the host cell.

A vector according to the present invention may further include an element such as a transcription enhancer sequence or translation enhancer sequence.

A vector according to the present invention may further have a DNA sequence that allows the vector to be replicated in the host cell. In a case where the host cell is a mammalian cell, the DNA sequence is, for example, an SV40 replication origin.

A vector according to the present invention may further have a selective marker. The selective marker is, for example, a drug resistance gene against a drug such as ampicillin, kanamycin, tetracycline, chloramphenicol, neomycin, or hygromycin.

An expression cassette according to the present invention is an expression cassette including (a) an expression regulatory region functional in an expression host and (b) a polynucleotide according to the present invention. An expression cassette according to the present invention may be in the form of the expression vector described above.

[4. Transformant and Method for Producing Transformant]

(Transformant and Method for Producing Transformant)

Introducing a polynucleotide according to the present invention, an expression cassette according to the present invention, or a vector according to the present invention into an appropriate host cell allows for establishment of a transformant. The transformant contains the full length of a polynucleotide according to the present invention or at least part of the polynucleotide, and allows for expression of any one of the fluorescent polypeptides of the present invention. Similarly, progeny of a transformant according to the present invention obtained by the use of the transformant also contains the full length of a polynucleotide according to the present invention or at least part of the polynucleotide, and allows for expression of any one of the fluorescent polypeptides of the present invention. In the transformant or its progeny, the full length of a polynucleotide according to the present invention or part of the polynucleotide is preferably integrated in a genome.

The description below uses the term "exogenous (foreign) nucleic acid molecule" of the present invention to collectively refer to a polynucleotide according to the present invention, an expression cassette according to the present invention, and a vector according to the present invention. The method for introducing an exogenous nucleic acid molecule of the present invention into a host cell may be selected depending on the kind of the host cell as described later as an example. Further, the method for obtaining progeny of a transformant according to the present invention may be selected depending on the kind of the transformant.

Examples of the host cell include a bacterial cell, a yeast cell, a fungal cell other than a yeast cell, and a higher eukaryotic cell. Examples of the higher eukaryotic cell include a plant cell and an animal cell. Examples of the animal cell include an insect cell, an amphibian cell, a reptile cell, an avian cell, a fish cell, and a mammalian cell. Examples of the bacterial cell include a Gram-positive bacterium such as *Bacillus* and *Streptomyces*; and a Gram-negative bacterium such as *Escherichia coli*. The yeast cell is, for example, a cell belonging to *Saccharomyces* or *Schizosaccharomyces*, and specific examples include *Saccharomyces cerevisiae* and *Saccharomyces kluyveri*. The fungal cell other than a yeast cell is, for example, a filamentous fungus cell. Examples of the filamentous fungus cell include a filamentous fungus cell belonging to *Aspergillus*, *Neurospora*, *Fusarium*, or *Trichoderma*. Examples of the insect cell include a silkworm cell. The mammalian cell is, for example, HEK293 cell, HeLa cell, COS cell, BHK cell, CHL cell, or CHO cell.

The method for transformation of a host cell may be selected as appropriate depending on, for example, the kind of the host cell. Examples of the method include protoplast method, method involving use of a competent cell, electroporation method, spheroplast method, acetic acid lithium method, calcium phosphate method, lipofection method, *Agrobacterium* method, and particle gun method. Another method for transformation of a host cell is, for example, a method for performing transformation by producing a host cell in which an exogenous nucleic acid molecule of the present invention has been integrated in a host chromosome. The integration of an exogenous nucleic acid molecule into a host chromosome can be performed by, for example, homologous recombination or heterologous recombination. Still another method for transformation of a host cell is, for example, a method of (i) cotransforming an exogenous nucleic acid molecule of the present invention and a baculovirus into a host cell to produce a recombinant baculovirus in a supernatant of the host cell culture and then (ii) infecting the host cell with the recombinant baculovirus to cause the host cell to produce a fluorescent polypeptide according to the present invention. Example methods of the cotransfection include calcium phosphate method and lipofection method.

The transformant is cultured or cultivated under a condition that allows the introduced exogenous nucleic acid molecule to be expressed.

The form of the transformant is not limited to a cell: The transformant may be, for example, tissue, organ, or individual that has been transformed with use of an exogenous nucleic acid molecule according to the present invention. A transformant other than a cell may preferably be of a non-human origin, and is preferably of a non-human origin particularly in a case where the transformant is an individual. The description below uses the term "non-human transgenic organism" to refer to a transformed individual of a non-human origin.

(Non-Human Transgenic Organism and Method for Production Thereof)

A non-human transgenic organism according to the present invention is, for example, a higher organism. Examples transgenic plants include transgenic forms of dicotyledons such as *Arabidopsis thaliana*; and monocotyledons such as *Brachypodium distachyon*, rice, wheat, and barley. Example transgenic animals include transgenic forms of animals such as zebrafish, mouse, rat, and pig.

The method for producing a non-human transgenic organism according to the present invention may simply be selected depending on the kind of the transgenic organism. Example methods for producing a transgenic animal include (i) a method of, on the basis of microinjection method or the like, introducing an exogenous nucleic acid molecule according to the present invention in vitro into a fertilized egg collected from a donor organism and (ii) a method of infecting in vitro a cell of an early developed germ derived from a donor organism with a viral vector such as a retrovirus. A transgenic plant may simply be produced by a method of, for example, (i) introducing an exogenous nucleic acid molecule according to the present invention into a plant cell on the basis of *Agrobacterium* method, particle gun method, electroporation method, or the like and then (ii) as necessary allowing the plant cell to form a callus for production of an individual transgenic plant.

The method for obtaining progeny of a non-human transgenic organism according to the present invention may also be selected depending on the kind of the non-human transgenic organism. An example method for a case of a higher organism is a method for obtaining progeny through mating. A method for a case where the higher organism is a plant may be a method of obtaining progeny with use of an asexual reproduction technique suitable for the kind of the plant.

(Clone of Non-Human Transgenic Organism and Method for Producing Clone)

The present invention covers in its scope producing a clone of a non-human transgenic organism according to the present invention, for example, with use of the non-human transgenic organism. A clone produced, as with the original non-human transgenic organism, contains the full length of a polynucleotide according to the present invention or at least part of the polynucleotide in a genome and allows for expression of any one of the fluorescent polypeptides according to the present invention. The term "clone" as used herein is a concept covering an embryonic cell clone and a somatic cell clone.

An example method for producing a clone is a method of nuclear transplantation, that is, a method of transplanting a cell nucleus of a donor into an enucleated unfertilized egg as a recipient. The cell nucleus of a donor may be (1) a somatic cell nucleus of the original non-human transgenic organism or (2) an embryonic cell nucleus derived from the original non-human transgenic organism. The cell nucleus of a donor contains the full length of a polynucleotide according to the present invention or at least part of the polynucleotide in a genome.

The method for nuclear transplantation of a cell nucleus of a donor is not particularly limited. Example methods include (1) a method of cell fusion between an enucleated unfertilized egg and a donor cell and (2) a method of introducing a donor cell into an enucleated unfertilized egg without cell fusion.

[5. Fusion Polypeptide According to Present Invention, Antibody Against Fluorescent Polypeptide]

(Fusion Polypeptide)

The present invention also covers in its scope a fusion polypeptide including a fluorescent polypeptide according to the present invention and another polypeptide (hereinafter referred to as "fusion polypeptide according to the present invention"). Examples of the fusion polypeptide include a fusion protein produced by expression of an expression cassette and/or vector according to the present invention; a fusion protein in which a protein is labeled with a fluorescent polypeptide according to the present invention; a fusion protein produced by fusing a fluorescent polypeptide according to the present invention with a predetermined peptide sequence for stabilizing fluorescence; and a FRET probe containing a fluorescent polypeptide according to the present invention and another fluorescent polypeptide. In other words, the kind of another polypeptide to be fused with a fluorescent polypeptide according to the present invention is not particularly limited. A fusion polypeptide according to the present invention may be chemically synthesized or produced with use of a gene recombination technique by a method similar to the method for producing a fluorescent polypeptide according to the present invention.

(Antibody)

The present invention also covers in its scope an antibody that is bonded specifically to a fluorescent polypeptide according to the present invention.

[6. Pluripotent Stem Cell and Method for Establishing Pluripotent Stem Cell]

The present invention also covers in its scope a method for establishing a pluripotent stem cell from a cell of a non-human transgenic organism according to the present invention. The method for establishing a pluripotent stem cell includes a step (reprogramming step) of establishing a pluripotent stem cell by introducing a reprogramming factor into a cell (herein referred to also as "starting cell") collected from a non-human transgenic organism according to the present invention or by treating such a cell with a reprogramming factor. The non-human transgenic organism is, for example, a non-human transgenic higher animal and is a non-human transgenic mammal in particular.

(Starting Cell)

The kind of a cell collected from a non-human transgenic organism according to the present invention is not particularly limited, but is preferably a somatic cell. The method for collecting a cell from the non-human transgenic organism may simply be a method suitable for the kind of the cell. The kind of the somatic cell may be any cell other than a germ cell, and may also be a somatic stem cell having a differentiation potency, an induced pluripotent stem cell, or a somatic cell differentiation-induced from either of the stem cells.

The origin of the somatic cell may be, for example, an individual at the embryonic stage or a mature individual.

(Reprogramming Factor)

The reprogramming factor is a factor that is introduced into a cell collected from the non-human transgenic organism or that is used for treatment of the cell to cause nucleus reprogramming of the cell. The nucleus reprogramming of the cell induces a pluripotent stem cell.

The reprogramming factor may be a "gene", a gene product of the "gene" (that is, a protein or RNA that the gene encodes), or "another factor" such as a drug. The reprogramming factor is preferably a "gene" or "protein", more preferably a "gene".

The reprogramming factor as a gene is, for example, at least one gene selected from the group consisting of Klf family gene, Oct family gene, Sox family gene, and Myc family gene. It is preferable to use at least one of Klf family gene and Oct family gene among others. Regarding Oct family gene, Klf family gene, Sox family gene, and Myc family gene, specific examples are mentioned in PCT International Publication WO2007/69666 (reference document).

Another example of the reprogramming factor as a gene is a factor for use in establishment of an iPS cell. Examples of such a factor include genes such as Lin family gene, Nanog gene, Tbx family gene, UTF1 gene, SALL family gene, Nr5a2 gene, Nr5a1 gene, Nr1i2 gene, Rem2 GTPase gene, TCL-1A gene, Esrr family gene, Prmt5 gene, and Glis family gene, and genes analogous to the above.

Other examples of the reprogramming factor as a gene include ES cell-specific miRNAs such as miR-291-3p, miR-294, and miR-295; miR-17-92, miR-106b-25, miR106a-363, miR-93, and miR-106b; mir-302 family miRNA; mir-200c, mir-302s, and mir-369s family miRNA.

Further, examples of the "another factor" include low-molecular compounds for use in establishment of an iPS cell such as arginine methyltransferase (PRMT) inhibitor, TGF-β inhibitor, GSK3 inhibitor, and lysine-specific demethylase 1 (LSD1) inhibitor, siRNA for p53 gene, embryonic cell histone, and histone chaperon.

(Reprogramming Step)

The above reprogramming step is performed in, for example, a culture environment that allows a starting cell and a pluripotent stem cell to proliferate and be maintained. The culture environment that allows a starting cell and a pluripotent stem cell to proliferate and be maintained is, for example, any of various culture environments in use for establishment of an induced pluripotent stem cell or a modified form of any of the culture environments.

In a case where the reprogramming factor is a gene, the reprogramming factor is introduced into a starting cell with use of, for example, a vector that contains the reprogramming factor in such a manner that the reprogramming factor can be expressed. The kind of the vector may be selected as appropriate depending on the kind of the starting cell. Examples of the vector include a plasmid vector and a viral vector (preferably an adenovirus vector, a retrovirus vector, or the like). Examples of the method for introducing the vector into a starting cell include electroporation method (Nucleic, Acids Res. 15, 1311-1326 (1987)), calcium phosphate method (Mol. Cell Biol. 7, 2745-2752 (1987)), and lipofection method (Cell 7, 1025-1037 (1994); Lamb, Nature Genetics 5, 22-30 (1993)).

In a case where the reprogramming factor is a protein, the reprogramming factor may be introduced into a starting cell by a method of adding, to a medium in which the starting cell is being cultured, the reprogramming factor so that the reprogramming factor is taken into the starting cell (see, for example, the following reference documents: (i) Zhou et al., Cell Stem Cell. 2009 May 8; 4(5): 381-4., (ii) Kim et al., Cell Stem Cell. 2009 Jun. 5; 4(6): 472-6., (iii) Japanese Patent Application Publication, Tokukai, No. 2010-110289 A (Publication Date: May 20, 2010), and (iv) Japanese Patent Application Publication, Tokukai, No. 2010-252786 A (Publication Date: Nov. 11, 2010) or by a method of establishing, in addition to the starting cell, a somatic cell containing the reprogramming factor abundantly (for example, a cell in which the reprogramming factor has been overexpressed) and fusing the two cells with use of a cell fusion technique. In a case where the reprogramming factor is a factor other than a gene or a protein (for example, a drug), the reprogramming factor may be introduced into a starting cell by a method of adding, to a medium in which the starting cell is being cultured, the reprogramming factor so that the reprogramming factor is taken into the starting cell or a method of treating a starting cell with the reprogramming factor.

(Pluripotent Stem Cell Produced)

The pluripotent stem cell produced exhibits at least multipotency, preferably having a state of exhibiting pluripotency or a state preceding the state. The term "multipotency" as used to describe the present invention refers to the ability to be differentiated into some cell strains such as a nervous system or a hematopoietic system. The term "pluripotency" as used to describe the present invention refers to the ability to be differentiated into any cell or tissue that constitutes an individual (but not an individual itself). An example pluripotent stem cell produced is a so-called "induced pluripotent stem cell". An "induced pluripotent stem cell" is a cell having a character close to that of an ES cell (embryonic stem cell). More specifically, the term "induced pluripotent stem cell" covers in its scope an undifferentiated cell that has pluripotency and the ability to proliferate maintaining undifferentiation state depending on the culture condition.

[7. Observation and the Like Involving Use of Fluorescent Polypeptide]

(Fluorescence Observation)

A fluorescent polypeptide and fusion polypeptide according to the present invention are not particularly limited in terms of application, and are widely usable in fluorescence observation. The fluorescence observation involves a step (fluorescence detecting step) of detecting fluorescence emission derived from a fluorescent polypeptide or fusion polypeptide according to the present invention.

An example of the fluorescence observation is a method including (i) a step (producing step) of producing a fluorescent polypeptide or fusion polypeptide according to the present invention in a cell and (ii) the above "fluorescence detecting step".

The above producing step can be carried out by, for example, a method described under [4. Transformant and Method for Producing Transformant] above. The above fluorescence detecting step is a step of detecting fluorescence emitted from a polypeptide or fusion polypeptide according to the present invention. The method for detecting fluorescence is not particularly limited, and is, for example, simply a method of measuring the presence or absence of fluorescence emission, distribution of fluorescence emission, fluorescence intensity, or the like temporarily or over time with use of a fluorescence detecting means such as a UV transilluminator or LED transilluminator; a fluorescence microscope; a fluorescence detector; or flow cytometry.

Another example of the fluorescence observation is a method including (i) a step (introducing step) of introducing a fluorescent polypeptide or fusion polypeptide according to the present invention into a cell and (ii) the above "fluorescence detecting step". Examples of the method for introducing the fluorescent polypeptide or the like into a cell include microinjection method, by which a purified fluorescent polypeptide or the like is injected into a cell.

One purpose of the fluorescence observation is to analyze localization or kinetics of a polypeptide. In a case where a fusion polypeptide is used that has been produced by fusing a fluorescent polypeptide according to the present invention with another polypeptide (herein referred to as "polypeptide X"), the localization or kinetics of the polypeptide X in a cell can be visualized for analysis. The kind of the polypeptide X is not particularly limited. Examples of the polypeptide X include a protein localized in a cell, a protein specific to an intracellular organelle, and a targeting signal. The targeting signal is, for example, a nuclear localization signal or a mitochondrial presequence.

Another purpose of the fluorescence observation is to analyze expression of a target gene. Carrying out the above producing step under the control of an expression regulatory sequence of the target gene allows for measurement of activity of the expression regulatory sequence. The activity of the expression regulatory sequence of the target gene reflects the level of expression of the target gene.

(Application of Fluorescence Observation: Evaluation of Test Substance)

Still another example of the fluorescence observation is an application to an evaluation method for evaluating the effect of a test substance on expression and/or localization of one or more target genes. The expression "localization of a target gene" intends to refer to localization of an expression product of the target gene.

The evaluation method includes at least the following steps (i) to (iv):

(i) an introducing step of introducing into cells a first nucleic acid molecule containing a polynucleotide (referred to as "polynucleotide according to the present invention") encoding a fluorescent polypeptide according to the present invention which fluorescent polypeptide may be fused with a first target gene (in which step the first nucleic acid molecule is operably linked to a first expression regulatory sequence so as to be under the control of the expression regulatory sequence), (ii) a culturing step of culturing the cells resulting from the introducing step in the presence of and in the absence of a test substance, (iii) a fluorescence detecting step of detecting respective fluorescence emissions in the cells, and (iv) an evaluating step of comparing the respective fluorescence emissions in the cells, produced in the presence of and in the absence of the test substance, so as to evaluate the effect of the test substance on expression and/or localization of the target gene.

The above term "target gene" refers to a gene selected for the purpose of confirming the effect of a test substance. In a case where there are a plurality of "target genes", the description herein may use terms such as "first target gene" and "second target gene" to discriminate the target genes from each other. Further, the term "test substance" refers to a substance that can act directly or indirectly on the "target gene". In a case where the test substance is, for example, a candidate compound for a therapeutic drug against a particular disease, the target gene is, for example, a gene related to the onset of the disease. Further, in a case where the test substance is, for example, a reprogramming factor, the target gene is, for example, a gene (such as Nanog) whose expression changes as the cell is reprogrammed. Regarding the reprogramming factor, refer to the [6. Pluripotent Stem Cell and Method for Establishing Pluripotent Stem Cell] section.

The above "first nucleic acid molecule" contains at least a polynucleotide according to the present invention. Expression of the first nucleic acid molecule is controlled by the first expression regulatory sequence. The first nucleic acid molecule may further contain as necessary a first target gene fused with a polynucleotide according to the present invention. In this case, a fusion polypeptide is produced in which an expression product of the first target gene and a fluorescent polypeptide according to the present invention are fused with each other. This allows for evaluation of localization of the first target gene during the evaluating step.

The "first expression regulatory sequence" may be an expression regulatory sequence of the above "first target gene". In this case, a polynucleotide according to the present invention is expressed in such a manner as to reflect an expression pattern of the first target gene. This allows for evaluation of the effect of a test substance on expression of the first target gene during the evaluating step. Further, the "first expression regulatory sequence" is preferably a promoter sequence.

The above "introducing step" and "culturing step" can each be carried out, for example, in accordance with a method described under [4. Transformant and Method for Producing Transformant] above.

The above "fluorescence detecting step" may simply measure the presence or absence of fluorescence emission, distribution of fluorescence emission, fluorescence intensity, or the like temporarily or over time with use of the above fluorescence detecting means. The fluorescence detecting step is carried out for both (i) a cell cultured in the presence of the test substance and (ii) a cell cultured in the absence of the test substance for comparison. During the "fluorescence detecting step", it is preferable to detect, for comparison, fluorescence emissions under a substantially identical condition except for whether the test substance is present.

The above "evaluating step" compares the respective fluorescence emissions of the cells obtained in the presence of and in the absence of the test substance. The "evaluating step" also evaluates, on the basis of the comparison results obtained, whether the test substance influences expression and/or localization of the target gene. In a case where, for example, there is no substantial difference in the results of the detection of the fluorescence emissions between the case where the test substance is present and the case where the test substance is absent, the "evaluating step" determines that the test substance does not influence expression and/or the like of the target gene. In a case where there is a significant difference in the results of the detection of the fluorescence emissions between the case where the test substance is present and the case where the test substance is absent, the "evaluating step" determines that the test substance does influence expression and/or the like of the target gene. The evaluation during the evaluating step includes evaluating whether and/or how much the test substance influences expression and/or localization of the target gene.

The above "introducing step" may as necessary introduce a second nucleic acid molecule into a cell in addition to the first nucleic acid molecule. The second nucleic acid molecule contains a polynucleotide encoding a fluorescent polypeptide (referred to as "second fluorescent polypeptide") different from the above "first nucleic acid molecule". Expression of the second nucleic acid molecule is controlled by a second expression regulatory sequence. The first nucleic acid molecule and the second nucleic acid molecule encode respective fluorescent polypeptides different from each other in terms of fluorescence property. This allows for detection of the two fluorescent polypeptides separately during the above fluorescence detecting step and evaluating step for evaluation.

The second nucleic acid molecule may contain as necessary a second target gene fused with a polynucleotide encoding the second fluorescent polypeptide. In this case, a fusion polypeptide is produced in which an expression product of the second target gene and the second fluorescent polypeptide are fused with each other. This allows for evaluation of localization of the second target gene during the evaluating step.

The "second expression regulatory sequence" may be an expression regulatory sequence of the above "second target gene". In this case, a polynucleotide encoding the second fluorescent polypeptide is expressed in such a manner as to reflect an expression pattern of the second target gene. This allows for evaluation of the effect of a test substance on expression of the second target gene during the evaluating step. Further, the "second expression regulatory sequence" is preferably a promoter sequence.

The "first target gene" and the "second target gene" are preferably genes different from each other. Further, the first expression regulatory sequence and the second expression regulatory sequence are preferably different from each other.

The above evaluation method is carried out ex vivo. The evaluation method is, in other words, carried out for an isolated cell or a cell contained in isolated tissue or the like.

[8. Method for Producing Fluorescent Polypeptide]

The present invention also provides a method for producing a mutated form of fluorescent polypeptide with use of a fluorescent polypeptide having any one of the respective amino acid sequences represented by SEQ IDs NO. 1, NO. 2, and NO. 5 to NO. 7.

Specifically, an aspect of a method according to the present invention for producing a fluorescent polypeptide is a method including:

(i) a step of preparing a mutated form of polypeptide in which at least one amino acid mutation has been caused to any amino acid other than amino acids 69 and 70 of the amino acid sequence represented by SEQ ID NO. 1, NO. 2, or NO. 5 to NO. 7, (ii) a comparing step of comparing the fluorescence property of the mutated form of polypeptide with the fluorescence property of the polypeptide before the mutation, and (iii) a selecting step of, on the basis of the comparison during the comparing step with the fluorescence property before the mutation, selecting a mutated form of polypeptide whose fluorescence property has changed.

The step of producing a mutated form of polypeptide is carried out in such a manner that in the amino acid sequence X—Y-G (where X is any amino acid) that forms a chromophore, —Y-G is fixed, and the other amino acid is mutated. This makes it possible to efficiently produce a mutated form of polypeptide having a maintained fluorescence property. Regarding the number of amino acids to be mutated and a method for causing amino acid mutation in each of SEQ IDs NO. 1, NO. 2, and NO. 5 to NO. 7, reference may be made to, for example, the [1. Polypeptide Having Fluorescence Property] section above.

The above selecting step selects a mutated form of polypeptide having a changed fluorescence property and excludes any mutated form of polypeptide that has completely lost its fluorescence property.

The above method for producing a mutated form of fluorescent polypeptide may be construed as a method for screening mutated forms of fluorescent polypeptides.

[9. Kit According to Present Invention]

(Kit)

A kit according to the present invention includes at least one kind selected from the group consisting of (1) a fluorescent polypeptide according to the present invention, (2) a polynucleotide encoding a fluorescent polypeptide according to the present invention, (3) an expression cassette according to the present invention, (4) a vector according to the present invention, (5) a transformant according to the present invention, and (6) a fusion polypeptide according to the present invention. In a case where the polynucleotide (2) is RNA, a kit according to the present invention can be used for an individual organism such as a human as a kit for primary expression involving no gene recombination.

A kit according to the present invention can be prepared with use of materials and techniques publicly known in the related technical field. Reagents such as a fluorescent polypeptide and a polynucleotide can each be prepared in a form suitable for preservation by dissolving the reagent in a suitable solvent. The solvent can be, for example, water, ethanol, or any of various publicly known buffer solutions.

A kit according to the present invention may further include as necessary at least one of, for example, various reagents and instruments (for example, a buffer solution, a test tube, and a pipet) and an instruction manual for the kit. The instruction manual for the kit provides information about, for example, a detection method according to the present invention which detection method is described under [7. Observation and the Like Involving Use of Fluorescent Polypeptide] above. A kit according to the present invention is used, for example, as a reagent or for diagnosis.

[10.]

The present invention may also be in any one mode below.

<1> A polypeptide having a fluorescence property, the polypeptide being defined in any one of (1) to (4) below: (1) A polypeptide having an amino acid sequence represented by SEQ ID NO. 1 or NO. 2, (2) A polypeptide having an amino acid sequence represented by SEQ ID NO. 1 or NO. 2 in which amino acid sequence 1 to 34 amino acids have been replaced, deleted, inserted, and/or added, (3) A polypeptide having a sequence identity of 85% or more with respect to the amino acid sequence represented by SEQ ID NO. 1 or NO. 2, and (4) A polypeptide encoded by a polynucleotide that hybridizes under a stringent condition with a polynucleotide having a sequence complementary to a polynucleotide that encodes the polypeptide defined in (1) above.

<2> The polypeptide according to <1>, wherein the polypeptide has a fluorescence quantum yield Φ of 0.6 or more or of 0.4 or more.

<3> A polynucleotide defined in any one of (1) to (4) below: (1) A polynucleotide encoding a polypeptide having an amino acid sequence represented by SEQ ID NO. 1 or NO. 2, (2) A polynucleotide encoding a polypeptide that has an amino acid sequence represented by SEQ ID NO. 1 or NO. 2 in which amino acid sequence 1 to 34 amino acids have been replaced, deleted, inserted, and/or added and that has a fluorescence property, (3) A polynucleotide encoding a polypeptide that has a sequence identity of 85% or more with respect to the amino acid sequence represented by SEQ ID NO. 1 or NO. 2 and that has a fluorescence property, and (4) A polynucleotide encoding a polypeptide that hybridizes under a stringent condition with a polynucleotide having a sequence complementary to the polynucleotide defined in (1) above and that has a fluorescence property.

<4> An expression cassette including: (a) an expression regulatory region functional in an expression host; and (b) a polynucleotide according to <3>.

<5> A vector including: a polynucleotide according to <3>; or an expression cassette according to <4>.

<6> A transformant including: a polynucleotide according to <3>; an expression cassette according to <4>; or a vector according to <5>.

<7> The transformant according to <6>, wherein the transformant is a non-human transgenic organism.

<6> A fusion polypeptide including: a polypeptide according to <1> or <2>; and another polypeptide.

<9> A method for fluorescence observation, the method including the steps of: producing, in a cell, a polypeptide according to <1> or <2> or a fusion polypeptide according to <8>; and observing fluorescence from the polypeptide or the fusion polypeptide.

<10> A method for evaluating effect of one or more test substances on expression and/or localization of one or more target genes in a cell, the method including the steps of: (i) introducing, into cells, a first nucleic acid molecule including a polynucleotide according to <3> which polynucleotide may be fused with a first target gene, the first nucleic acid molecule being operably linked to a first expression regulatory sequence so as to be under control of the first expression regulatory sequence; (ii) culturing the cells, resulting from the step (i), in presence of and in absence of the one or more test substances; (iii) detecting respective fluorescence emissions in the cells; and (iv) comparing the respective fluorescence emissions in the cells, produced in the presence of and in the absence of the one or more test substances, so as to evaluate the effect of the one or more test substances on the expression and/or localization of the one or more target genes.

<11> The method according to <10>, wherein the step (i) further includes introducing, into the cells, a second nucleic acid molecule including a polynucleotide encoding a fluorescent polypeptide different from the first nucleic acid molecule, the second nucleic acid molecule being operably linked to a second expression regulatory sequence so as to be under control of the second expression regulatory sequence.

<12> A method for producing a transformant including, in a cell, all or part of a polynucleotide according to <3>, the method including the step of introducing, into a cell, a polynucleotide according to <3>, an expression cassette according to <4>, or a vector according to <5>.

<13> A transformant produced by a method according to <12> or progeny of the transformant.

<14> A method for producing a non-human transgenic organism including, in a cell, all or part of a polynucleotide according to <3>, the method including the step of introducing, into a fertilized egg collected from a donor cell, a polynucleotide according to <3>, an expression cassette according to <4>, or a vector according to <5>.

<15> A non-human transgenic organism produced by a method according to <14> or progeny of the non-human transgenic organism.

<16> A method for establishing a pluripotent stem cell, the method including the steps of: collecting a cell from a non-human transgenic organism or progeny thereof according to <15>; and introducing a reprogramming factor into the cell.

<17> A kit including: a polypeptide according to <1> or <2>; a polynucleotide according to <3>; an expression cassette according to <4>; a vector according to <5>; a transformant according to <6> or <7>; or a fusion polypeptide according to <8>.

The present application claims priority on Japanese patent application Tokugan 2013-173850 (basic application) filed on Aug. 23, 2013, and the entire content of the basic application is incorporated in the present specification.

The description below deals with the present invention in detail on the basis of Examples. The present invention is, however, not limited by the Examples.

EXAMPLES

1. Cloning of Gene Derived from *Montipora monasteriata*

(Materials and Method)

*Montipora monasteriata* was fractured with use of a multi-bead shocker (Yasui Kikai Corporation), and total RNA was then extracted with use of TRIzol (Invitrogen). Next, mRNA was purified from the extracted total RNA with use of Oligotex-dT30<super> (Takara Bio Inc.). After that, a cDNA library was prepared from the mRNA with use of SuperScript Plasmid System with Gateway Technology for cDNA Synthesis and Cloning (Invitrogen). A primer represented by SEQ ID NO. 11 was used for reverse transcription involving use of the mRNA as a template. The cDNA prepared was inserted into *Escherichia coli* expression vector pFASTSET (that is, a vector prepared by replacing a multicloning site of pRSET (Invitrogen) with a multicloning site of pFastBac (Invitrogen)), then introduced into *Escherichia coli* JM109 (DE3) (Promega), and cultured on a plate of an LB solid medium containing ampicillin. As a result, colonies were obtained. The colonies obtained were each irradiated with light of a UV illuminator, a blue LED, and a green LED to see whether the colony emitted fluorescence. Colonies from each of which fluorescence was seen to be emitted were then each cultured in a liquid medium. After that, DNA was extracted from the *Escherichia coli* culture, and its base sequence was determined.

(Results)

Two colonies that emitting light were obtained. From these colonies, clones of two fluorescent proteins (1-29 and 1-41) were obtained. Further, one colored colony was obtained, and a clone of a pigment protein was obtained. A BLAST search indicated that the two fluorescent proteins were novel proteins, whereas the pigment protein was an already known protein.

2. Expression of Proteins 1-29 and 1-41 in *Escherichia Coli*

(Materials and Method)

<Preparation of Vector for *Escherichia coli* Expression>

DNA of 1-29 was amplified through a PCR with use of a forward primer represented by SEQ ID NO. 12 and a reverse primer represented by SEQ ID NO. 13. Further, DNA of 1-41 was amplified through a PCR involving use of a forward primer represented by SEQ ID NO. 14 and a reverse primer represented by SEQ ID NO. 15. Respective DNA fragments resulting from the PCRs in each of which DNA fragments a KpnI site was added to an N-terminus and an EcoRI site was added to a C-terminus were each inserted into *Escherichia coli* expression vector pRSET (Invitrogen). This prepared a plasmid DNA for *Escherichia coli* expression.

<Expression and Culture of *Escherichia coli* Expression Vector in *Escherichia coli*, and Purification of Protein>

The above plasmid DNA for *Escherichia coli* expression was introduced into *Escherichia coli* strain JM109 (DE3) (Promega) by heat shock method, and was inoculated onto a plate of an LB solid medium containing ampicillin. As a result, colonies were obtained. The colonies obtained were inoculated into an LB liquid medium, and were cultured at room temperature for three days. After the culture, the medium was centrifuged with use of a centrifuge to collect bacterial cells of *Escherichia coli*. Then, the bacterial cells of *Escherichia coli* were disrupted by freezing and thawing method, and the lysate was centrifuged with use of a centrifuge to obtain a supernatant. The supernatant was subjected to a His-tag purification with use of a Ni-NTA column. Next, a buffer exchange was carried out with use of a Sephadex G-25 column.

<Measurement of Protein Concentration>

The protein concentration was measured by Bradford method with use of BSA (bovine serum albumin) as a standard solution.

3. Analysis of Fluorescence Properties of Proteins 1-29 and 1-41

(Materials and Method)

<Measurements of Absorption Spectrums, Fluorescence Spectrums, and Quantum Yields>

To analyze the respective fluorescence properties of proteins 1-29 and 1-41, measurements of the absorption spectrums, the fluorescence spectrums, and the quantum yields were performed.

Each protein was suspended with use of a spectro photometer (Hitachi High-Technologies Corporation) to have 40 μM in 50 mM of HEPES-NaOH (pH 7.4), and the absorption spectrum was then measured. Further, each protein was suspended with use of SynergyMx (Biotek) to have 2 μM in 50 mM of HEPES-NaOH (pH 7.4), and the fluorescence spectrum was then measured. In addition, each protein was suspended with use of an absolute PL quantum yield measuring system (Hamamatsu Photonics K.K.) to have 2 μM in 50 mM of HEPES-NaOH (pH 7.4), and the quantum yield was then measured. The results are shown in FIG. 1. Further, the measurement results obtained are summarized in Table 1.

(Results)

FIG. 1 shows the respective fluorescence properties of proteins 1-29 and 1-41.

TABLE 1

| Clone name | Maximum absorption wavelength (nm) | Molar extinction coefficient (M$^{-1}$cm$^{-1}$) | Maximum excitation wavelength (nm) | Maximum fluorescence wavelength (nm) | Quantum yield (pH 7.4) |
|---|---|---|---|---|---|
| 1-29 | 575 | 40,300 | 574 | 608 | 0.63 |
| 1-41 | 573 | 43,800 | 572 | 592 | 0.76 |

4. Analysis of *Mutans* of 1-29 and *Mutans* of 1-41

(Materials and Method)

<Preparation of Mutants of 1-29 and Mutants of 1-41 Through Mutation Introduction, Preparation of Vectors for *Escherichia Coli* Expression for Mutants of 1-29 and Mutants of 1-41, and Expression and Culture in *Escherichia Coli* and Purification of Protein>

To obtain monomeric mutants, mutation was introduced randomly by random mutagenesis method and point mutation method into 1-29 and 1-41 by using, as templates, *Escherichia coli* expression vectors of wild-type 1-29 and 1-41 obtained under [2. Expression of Proteins 1-29 and 1-41 in *Escherichia coli*] above. As a result, a plurality of mutants of 1-29 and mutants of 1-41 were obtained. For each mutant, protein expression and culture in *Escherichia coli* with use of *Escherichia coli* expression vector and purification of the protein were performed by a method similar to a method described under [2. Expression of Proteins 1-29 and 1-41 in *Escherichia coli*].

Whether a mutant had been monomerized was determined by (i) irradiating, with UV light, a gel in which the mutant of protein had been electrophoresed by Pseud-Native-PAGE electrophoresis and (ii) checking fluorescence emission of a protein having a molecular weight corresponding to a monomer. For clones for each of which monomerization had been confirmed, mutation of the amino acid sequence was examined. The results are shown in (a) of FIG. 2.

(Results)

Figure 2:
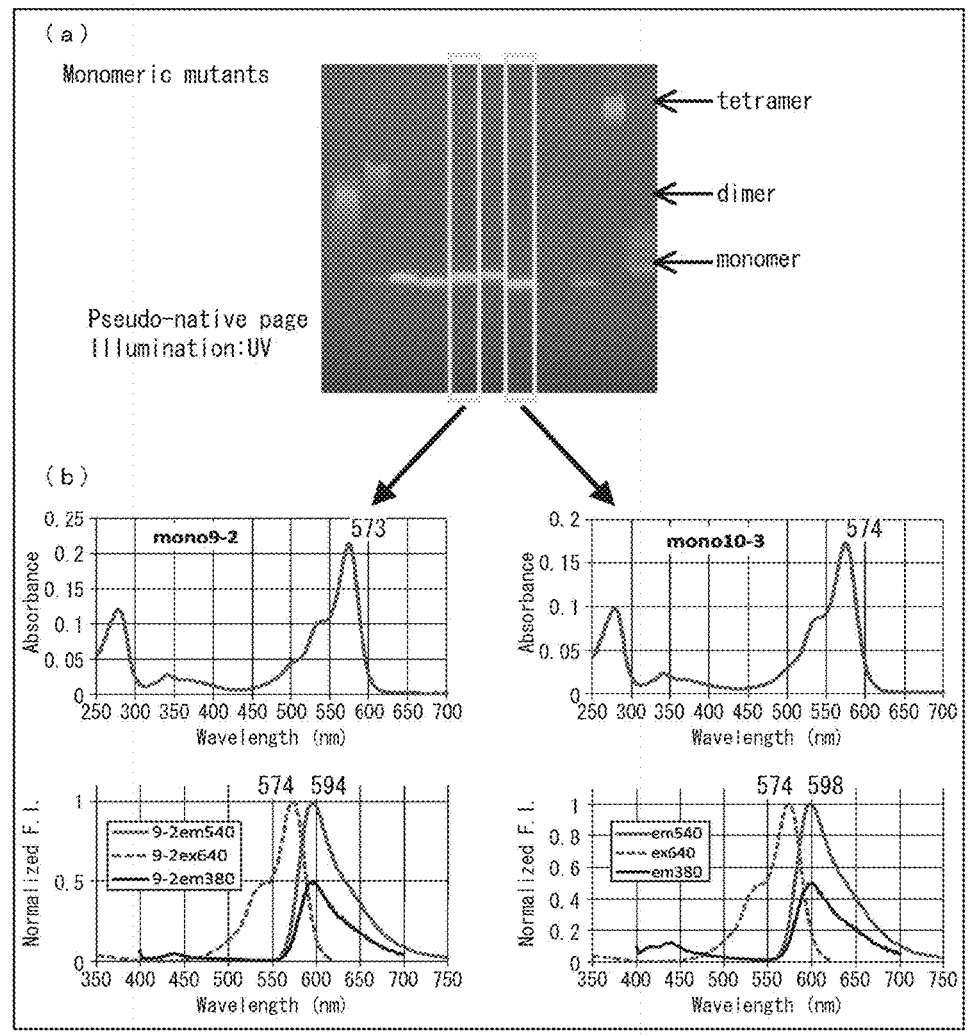
FIG. 2 provides an image and graphs that show expression and fluorescence properties of monomeric mutants in *Escherichia coli* in an Example of the present invention.

FIG. 2 shows expression of monomeric mutants in *Escherichia coli* and fluorescence properties of the monomeric mutants. (a) of FIG. 2 is an image observed of a mutant of protein by irradiating, with UV light by use of a UV transilluminator, a gel in which the mutant of protein had been electrophoresed by Pseud-Native-PAGE electrophoresis.

As shown in (a) of FIG. 2, several monomeric mutants were obtained. Among those mutants, 9-2B, 9-4, and 10-3 emitted particularly strong fluorescence.

The respective amino acid sequences of 9-2B, 9-4, and 10-3 are shown in SEQ IDs NO. 5, NO. 6, and NO. 1, respectively.

10-3 (SEQ ID NO. 1), monomeric fluorescent polypeptide A has the following main fluorescence properties:
Maximum excitation wavelength (nm): 574
Maximum fluorescence wavelength (nm): 598 (red)
Molar extinction coefficient (M$^{-1}$ cm$^{-1}$): 49500
Quantum yield (%): 66 (pH 7.4)
Fluorescence lifetime (nanoseconds):
pH sensitivity: pH 6 or more, where the fluorescence intensity is stable at a pH 6 to 11 in particular, with no sensitivity.

9-2B (SEQ ID NO. 5), monomeric fluorescent polypeptide A has the following main fluorescence properties:
Maximum excitation wavelength (nm): 573
Maximum fluorescence wavelength (nm): 594 (red)
Molar extinction coefficient (M$^{-1}$ cm$^{-1}$): 60300
Quantum yield (%): 68 (pH 7.4)
Fluorescence lifetime (nanoseconds):
pH sensitivity: pH 6 or more, where the fluorescence intensity is stable at a pH of 6 to 11 in particular, with no sensitivity.

9-4 (SEQ ID NO. 6), monomeric fluorescent polypeptide A has the following main fluorescence properties:
Maximum excitation wavelength (nm): 573
Maximum fluorescence wavelength (nm): 610 (red)
Molar extinction coefficient (M$^{-1}$ cm$^{-1}$): 44100
Quantum yield (%): 73 (pH 7.4)
Fluorescence lifetime (nanoseconds):
pH sensitivity: pH 6 or more, where the fluorescence intensity is stable at a pH 6 to 11 in particular, with no sensitivity.

5. Analysis of Fluorescence Properties of Monomerized Mutant Proteins of 1-29 and 1-41

(Materials and Method)

<Measurements of Absorption Spectrums, Fluorescence Spectrums, and Quantum Yields of Mutant Proteins of 1-29 and 1-41>

To analyze the respective fluorescence properties of monomeric mutant proteins of 1-29 and 1-41, measurements of the absorption spectrums, the fluorescence spectrums, and the quantum yields were performed.

Each protein was suspended with use of a spectro photometer (Hitachi High-Technologies Corporation) to have 40 μM in 50 mM of HEPES-NaOH (pH of 7.4), and the absorption spectrum was then measured. Further, the molar extinction coefficient was calculated at the maximum absorption wavelength.

Each protein was suspended with use of SynergyMx (BioTek) to have 2 μM in 50 mM of HEPES-NaOH (pH of 7.4), and the fluorescence spectrum was then measured. Further, each protein was suspended with use of an absolute PL quantum yield measuring system (Hamamatsu Photonics K.K.) to have 2 μM in 50 mM of HEPES-NaOH (pH of 7.4), and the quantum yield was then measured. Similar measurements of publicly known fluorescent proteins mStrawberry and TagRFP, were performed and the measurement values were compared with those for mutants of 1-29 and 1-41. TagRFP was adjusted to have an absorption value of 0.1 at 525 nm, whereas any other protein was adjusted to have an absorption value of 0.1 at 540 nm. The results are shown in (b) of FIG. 2 and FIG. 3. Further, the measurement results obtained are summarized in Table 2.

(Results)

FIG. 2 shows expression of monomeric mutants in *Escherichia coli* and fluorescence properties of the monomeric mutants. (b) of FIG. 2 provides graphs that show the respective fluorescence properties of two monomeric clones (9-2B and 10-3). The upper graphs show the respective absorption spectrums of the two monomeric clones. The lower graphs show the respective excitation spectrums (EX) and fluorescence spectrums (EM) of the two monomeric clones. The fluorescence intensity of an excitation spectrum shows a value obtained in a case where the wavelength of detection light was fixed at 640 nm. The two fluorescence spectrums show respective values obtained in a case where the wavelength of excitation light is 540 nm (upper spectrum) and in a case where the wavelength of excitation light is 380 nm (lower spectrum).

Figure 3:
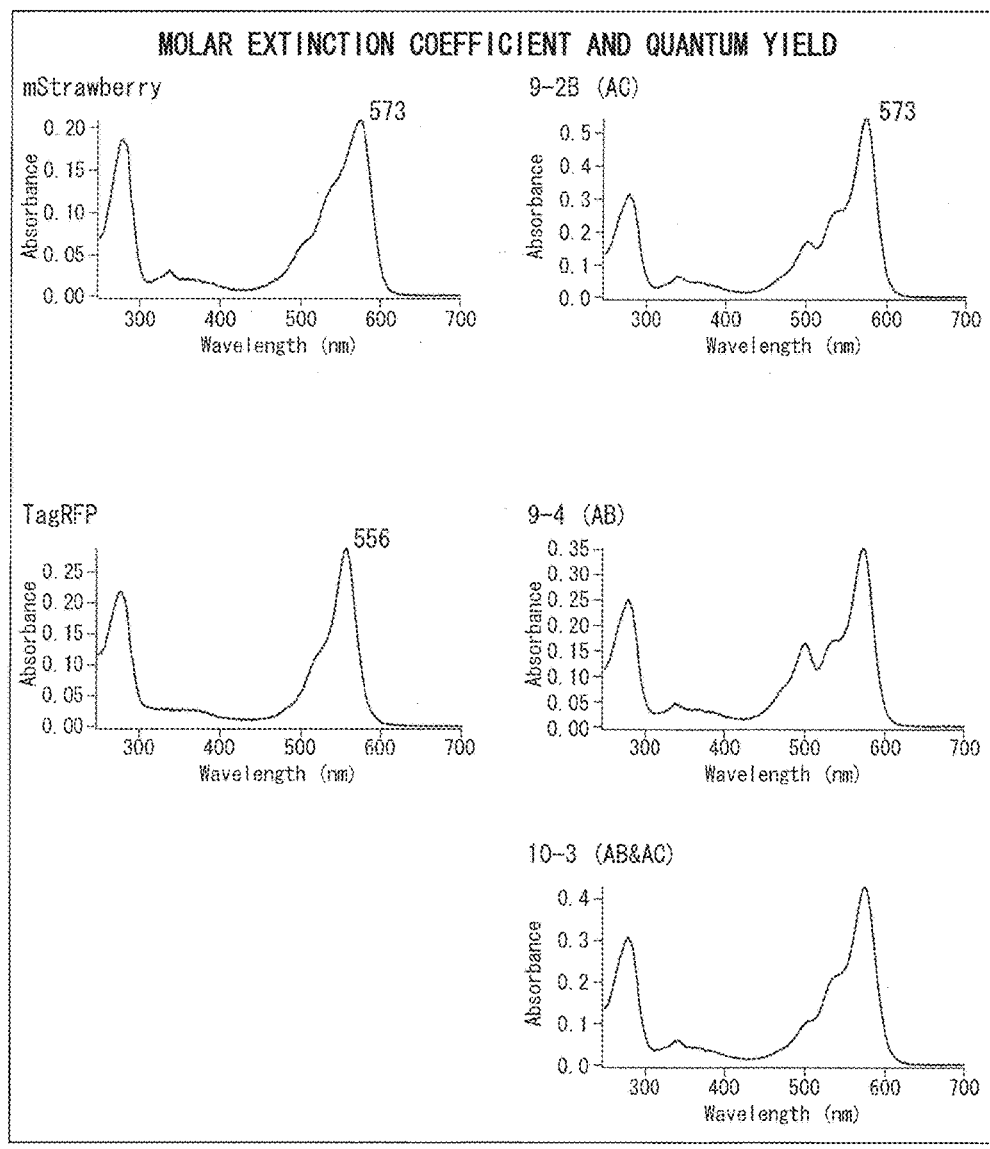
FIG. 3 provides graphs that show the respective fluorescence properties of three monomeric mutants in an Example of the present invention, the graphs showing the respective absorption spectrums of the three mutants.

FIG. 3 provides graphs that show respective fluorescence properties of three monomeric mutants, the graphs showing the respective absorption spectrums of the three mutants. mStrawberry and TagRFP were used as publicly known red fluorescent proteins.

The molar extinction coefficients calculated were 52000 for mStrawberry (90000 according to the report of Shaner et al., 2004 Nature Biotechnolgy), 48700 for TagRFP (100000 according to the report of Merzlyak et al., 2007 Nature Methods), 60300 for 9-2B, 44100 for 9-4, and 49500 for 10-3.

The quantum yields were as follows: 0.31 for mStrawberry at a pH 7.4 (0.22 according to the report of Shaner et al., 2004 Nature Biotechnolgy) and 0.52 for TagRFP at a pH 7.4 (0.48 according to the report of Merzlyak et al., 2007 Nature Methods), whereas 0.68 for 9-2B at a pH 7.4, 0.73 for 9-4 at a pH of 7.4, and 0.66 for 10-3 at a pH 7.4.

The above comparisons confirmed an excellent fluorescence property of a fluorescent polypeptide of the present invention.

Next, how early a fluorescent polypeptide of the present invention would start to emit light in an *Escherichia coli* (JM109DE3) colony was compared with cases of mStrawberry and TagRFP. *Escherichia coli* expression vectors were introduced into *Escherichia coli* in a manner similar to the above, and were cultured at 37° C. for 17 hours. Then, the respective fluorescence emissions were examined. This confirmed that only a small number of colonies had stated to emit light for mStrawberry, whereas a large number of colonies had stated to emit light for TagRFP and a fluorescent polypeptide of the present invention.

TABLE 2

| Clone name | Maximum absorption wavelength (nm) | Molar extinction coefficient (M$^{-1}$cm$^{-1}$) | Maximum excitation wavelength (nm) | Maximum fluorescence wavelength (nm) | Quantum yield (pH 7.4) |
|---|---|---|---|---|---|
| 9-2B | 573 | 60,300 | 573 | 594 | 0.68 |
| 9-4 | 573 | 44,100 | 573 | 594 | 0.73 |
| 10-3 | 574 | 49,500 | 574 | 598 | 0.66 |

6. Analysis of pH Sensitivities of Monomerized Mutant Proteins of 1-29 and 1-41

(Materials and Method)

For a purified protein of each of monomeric mutants of 1-29 and 1-41, the fluorescence intensities were measured with use of SynergyMx (Biotek) in 50 mM of CH$_3$COONa—CH$_3$COOH (pH of 4.0 and pH of 5.0), 50 mM of KH$_2$PO$_4$—NaOH (pH 6.0), 50 mM of HEPES-NaOH (pH 7.0), 50 mM of Tricine-NaOH (pH of 8.0), 50 mM of Glycine-NaOH (pH of 9. and pH 10.0), and 50 mM of Na$_2$HPO$_4$—NaOH (pH of 11.0). The measurement values obtained were normalized on the basis of the largest value.

(Results)

Figure 4:
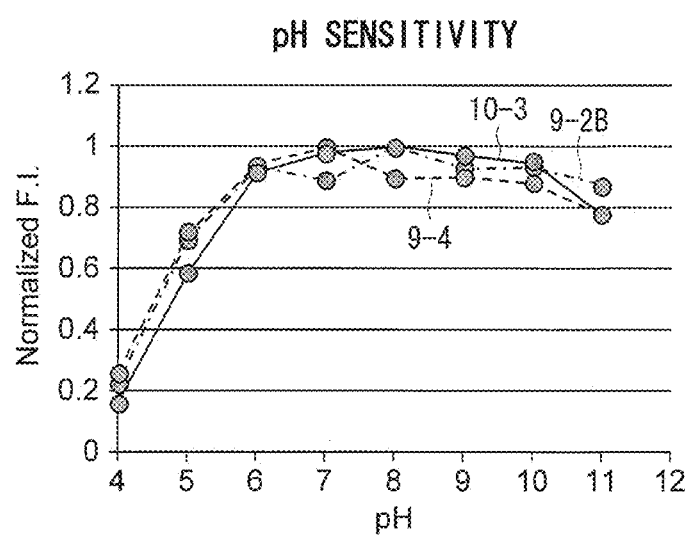
FIG. 4 is a graph that shows pH sensitivities of the respective fluorescence intensities of three monomeric mutants in an Example of the present invention.

FIG. 4 shows pH sensitivities of the respective fluorescence intensities of the three monomeric mutants.

The pH sensitivities were as follows: pKa=4.5 for clones 9-2B and 9-4, and pKa=4.8 for 10-3.

7. Analysis of Fluorescence Stabilities of Monomerized Mutants of 1-29 and 1-41

(Materials and Method)

Respective genes of 9-2B, 9-4, 10-3, mStrawberry, and TagRFP were each introduced into a HeLa cell with use of Lipofectamine 2000 reagent (Invitrogen). One (1) day later, the cells were observed with use of a fluorescence microscope (Objective lens: UplanSApox60, excitation: 562 nm/40, fluorescence: 624 nm/40, dichroic mirror: 601 nm, ND: 1%, elapsed time: every 3 minutes). The cells were irradiated with excitation light under an identical condition, and were examined for bleaching. The results are shown in FIGS. 5A and 5B.

(Results)

Figure 5A:
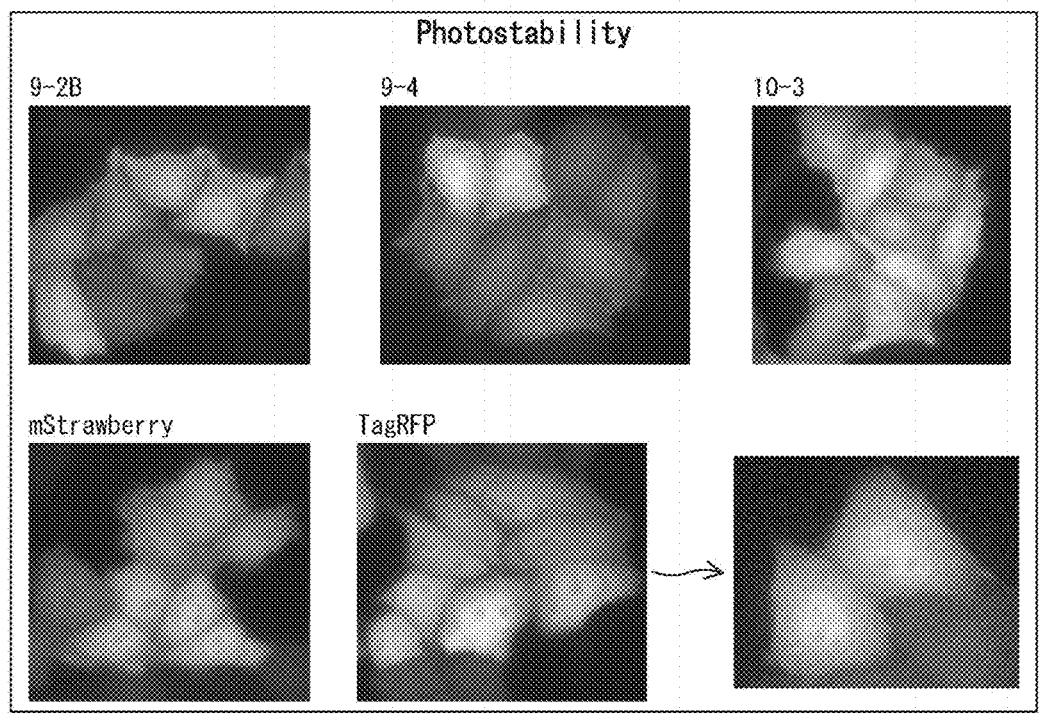
FIG. 5A provides images that show the respective fluorescence stabilities of three monomeric mutants in an Example of the present invention.
Figure 5B:
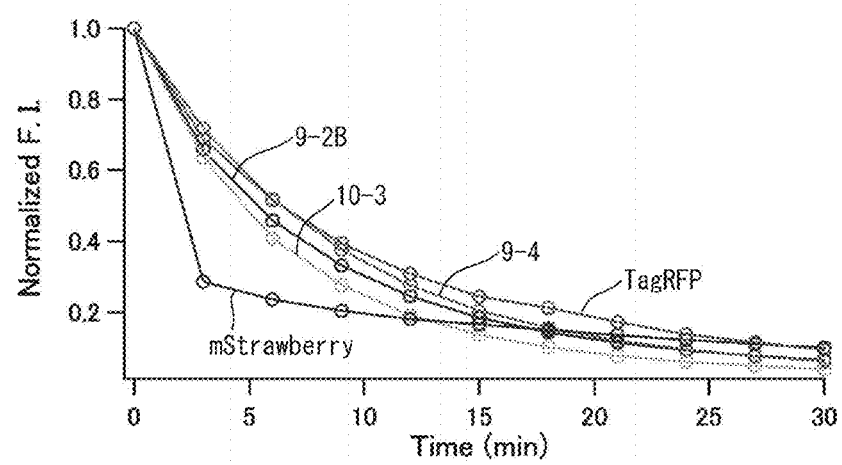
FIG. 5B is a graph corresponding to FIG. 5A which graph shows the respective fluorescence stabilities of the three monomeric mutants in an Example of the present invention.

FIGS. 5A and 5B provide images (FIG. 5A) and a graph (FIG. 5B) that show stability of fluorescence of the three monomeric mutants.

9-2B, 9-4, and 10-3 were each expressed in a mammal cell successfully. For TagRFP, spots were seen that indicated the possibility of aggregation of TagRFP in the cytoplasm (see the lower right image of FIG. 5A). Such spots were not observed in 9-2B, 9-4, or 10-3, as well as mStrawberry.

The graph, which shows a change in fluorescence intensity along the temporal axis, indicates that bleaching occurs more slowly in 9-2B, 9-4, and 10-3 than mStrawberry.

8. Analysis of Fluorescence Properties of Mutant Proteins of 1-29 and 1-41 with Shifted Fluorescence Wavelengths (Materials and Method)

Mutation was introduced randomly by random mutagenesis method and point mutation method in a manner similar to the manner described under [4. Analysis of Mutants 1-29 and 1-41] into 1-29 and 1-41 by using, as templates, *Escherichia coli* expression vectors of wild-type 1-29 and 1-41 obtained under [2. Expression of Proteins 1-29 and 1-41 in *Escherichia coli*] above. As a result, a plurality of mutants of 1-29 and mutants of 1-41 were obtained. For each mutant, expression and culture of *Escherichia coli* expression vector in *Escherichia coli* and purification of the protein were performed by a method similar to the method described under [2. Expression of Proteins 1-29 and 1-41 in *Escherichia coli*]. For the protein of each mutant, measurements of the absorption spectrums, the fluorescence spectrums, and the quantum yields were performed by a method similar to the method described under [5. Analysis of Fluorescence Properties of Monomerized Mutant Proteins of 1-29 and 1-41]. The results are shown in FIG. 6.

(Results)

Figure 6:
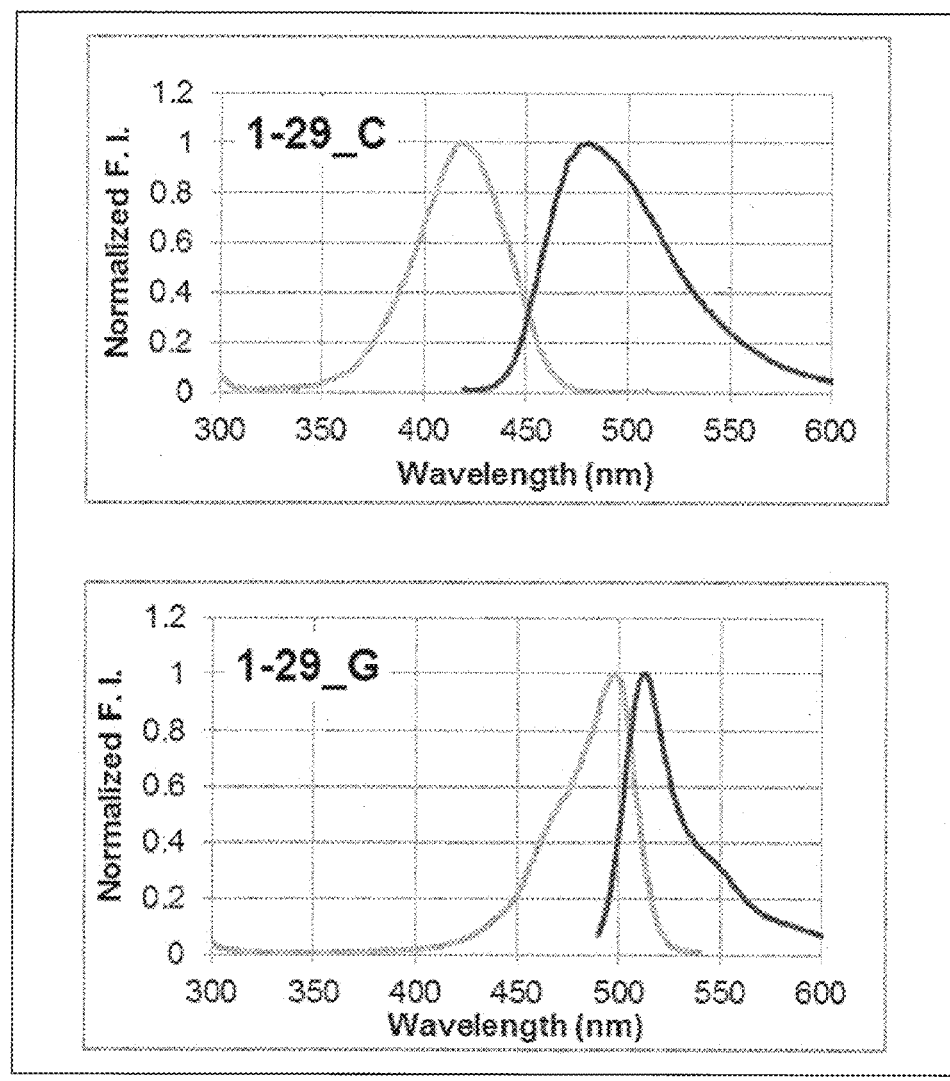
FIG. 6 provides graphs that show a shift in the fluorescence wavelength of each of two mutants in an Example of the present invention.

FIG. 6 provides graphs that show a shift in the fluorescence wavelength of each of the two mutants.

Analysis showed that among the plurality of mutants of 1-29 and mutants of 1-41, 1-29C (SEQ ID NO. 7) and 1-29G (SEQ ID NO. 2), which were mutants of 1-29, had respective fluorescence wavelengths shifted in the vicinity of 420 nm and 500 nm, respectively. These mutants make it possible to select a fluorescence wavelength in correspondence with a purpose.

9. Analysis of Other Mutants

<Preparation of Mutants of 1-41 Through Mutation Introduction, Preparation of Vectors for *Escherichia Coli* Expression for Mutants of 1-41, and Expression and Culture in *Escherichia Coli* and Purification of Protein>

Mutation was introduced randomly by random mutagenesis method and point mutation method by using, as a template, an *Escherichia coli* expression vector of wild-type protein 1-41 obtained under [2. Expression of Proteins 1-29 and 1-41 in *Escherichia coli*] above. As a result, a plurality of mutants of 1-41 were obtained. For each mutant, expression and culture of *Escherichia coli* expression vector in *Escherichia coli* and purification of the protein were performed by a method similar to the method described under [2. Expression of Proteins 1-29 and 1-41 in *Escherichia coli*].

Whether a mutant obtained had been monomerized was determined by (i) irradiating, with UV light, a gel in which the mutant of protein had been electrophoresed by Pseud-Native-PAGE electrophoresis and (ii) checking fluorescence emission of a protein having a molecular weight corresponding to a monomer. For clones for each of which monomerization had been confirmed, mutation of the amino acid sequence was examined. A new mutant obtained (referred to as "mAzalea") had an amino acid sequence represented by SEQ ID NO. 16, and the coding region of a gene encoding mAzalea had a base sequence represented by SEQ ID NO. 17.

10. Analysis of Fluorescence Property of mAzalea (Materials and Method)

<Measurements of Absorption Spectrum, Fluorescence Spectrum, and Quantum Yield of mAzalea>

To analyze the fluorescence property of mAzalea obtained under [9. Analysis of Other Mutants] above, measurements of the absorption spectrum, the fluorescence spectrum, and the quantum yield were performed.

The protein was suspended with use of a spectro photometer (Hitachi High-Technologies Corporation) to have 40 μM in 50 mM of HEPES-NaOH (pH of 7.4), and the absorption spectrum was then measured. Further, the molar extinction coefficient was calculated at the maximum absorption wavelength. The molar extinction coefficient was calculated, with reference to a chromophore of a mature GFP having a molar extinction coefficient of 44000 ($M^{-1}$ $cm^{-1}$) at 446 nm in a case where the GFP was denatured with use of 1 M of NaOH, from the ratio between (i) the absorption value of mAzalea at 446 nm for a case where mAzalea was denatured and (ii) the peak absorption value of mAzalea at a pH 7.4. mAzalea (fluorescent protein) was suspended with use of SynergyMx (BioTek) to have 2 μM in 50 mM of HEPES-NaOH (pH of 7.4), and the fluorescence spectrum was then measured. Further, mAzalea was suspended with use of an absolute PL quantum yield measuring system (Hamamatsu Photonics K.K.) to have 2 μM in 50 mM of HEPES-NaOH (pH of 7.4), and the quantum yield was then measured. mAzalea was suspended to have 2 μM so as to be adjusted to have an absorption value of 0.1 at 540 nm. The results are shown in FIG. 7.

(Results)

Figure 7:
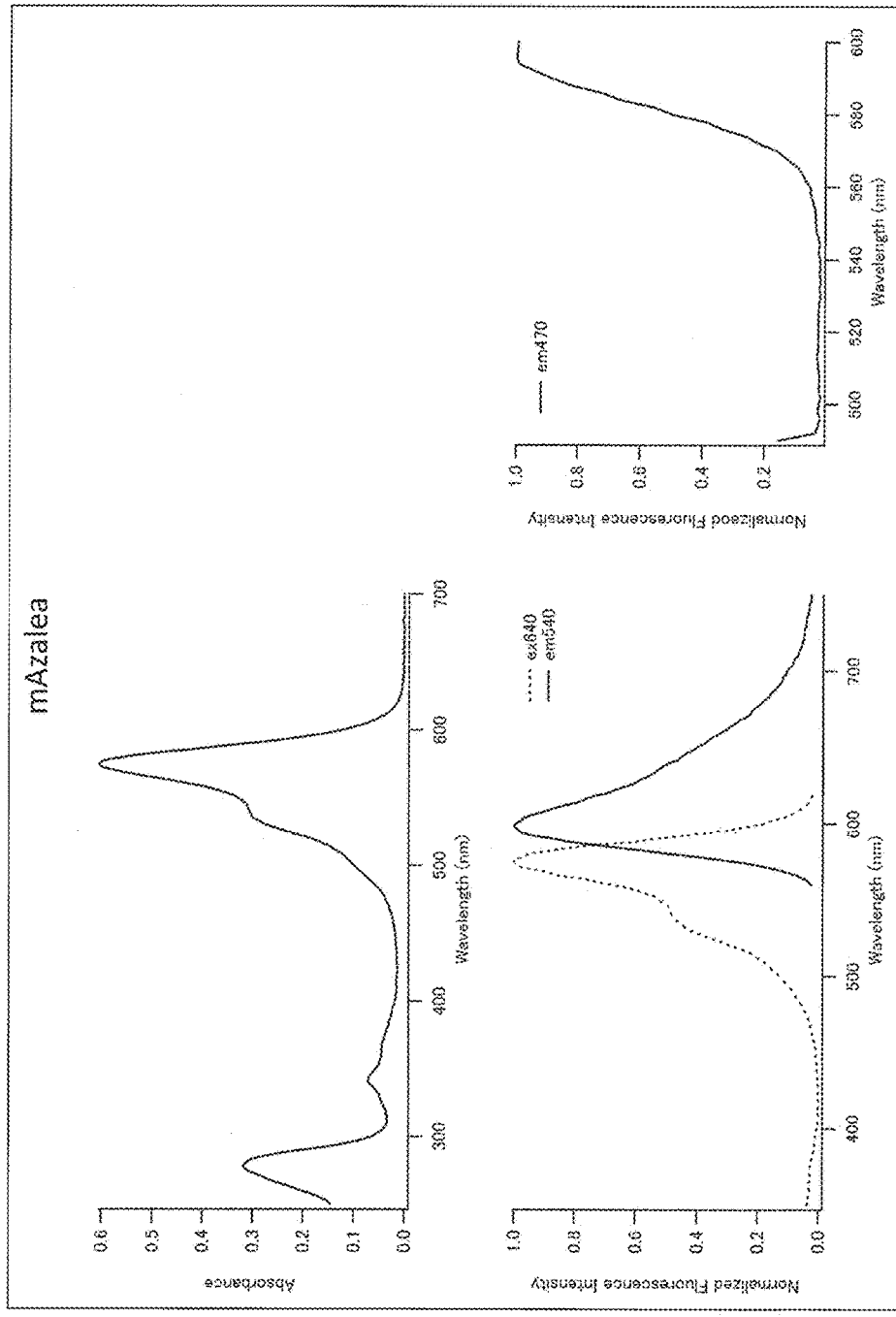
FIG. 7 provides graphs that show the fluorescence property of mAzalea, which is a protein according to another Example of the present invention.

FIG. 7 shows the fluorescence property of mAzalea. The upper graph in FIG. 7 shows the absorption spectrum of mAzalea. The two lower graphs in FIG. 7 show the excitation spectrum (ex640: indicated by a dotted line) and fluorescence spectrum (em540, em470: indicated by a solid line) of mAzalea. The fluorescence intensity of an excitation spectrum shows a value obtained in a case where the wavelength of detection light was fixed at 640 nm. The two fluorescence spectrums (em540, em470) show respective values obtained in a case where the wavelength of excitation light was 540 nm and in a case where the wavelength of excitation light was 470 nm.

As a result of analyzing the fluorescence property, mAzalea has the following main properties at a pH of 7.4:
Absorption peak (nm): 575
Maximum excitation wavelength (nm): 574
Maximum fluorescence wavelength (nm): 598 (red)
Molar extinction coefficient ($M^{-1}$ $cm^{-1}$): 103200
Quantum yield (%): 49
pH sensitivity: pH of 5 or more and 9 or less, where the fluorescence intensity is stable at a pH of 6 to 8 in particular, with no sensitivity. If the pH is less than 5 or more than 9, the fluorescence intensity decreases largely.

11. Analysis of PH Sensitivity of mAzalea (Materials and Method)

For a purified protein of mAzalea, the fluorescence intensity was measured with use of SynergyMx (Biotek) in 50 mM of $CH_3COONa$—$CH_3COOH$ (pH of 4.0 and pH of 5.0), 50 mM of $KH_2PO_4$—NaOH (pH of 6.0), 50 mM of HEPES- NaOH (pH of 7.0), 50 mM of Tricine-NaOH (pH of 8.0), 50 mM of Glycine-NaOH (pH of 9.0 and pH of 10.0), and 50 mM of $Na_2HPO_4$—NaOH (pH of 11.0). The measurement values obtained were normalized on the basis of the largest value. Further, the absorption spectrum was also measured with use of a spectro photometer (Hitachi High-Technologies Corporation).

(Results)

Figure 8:
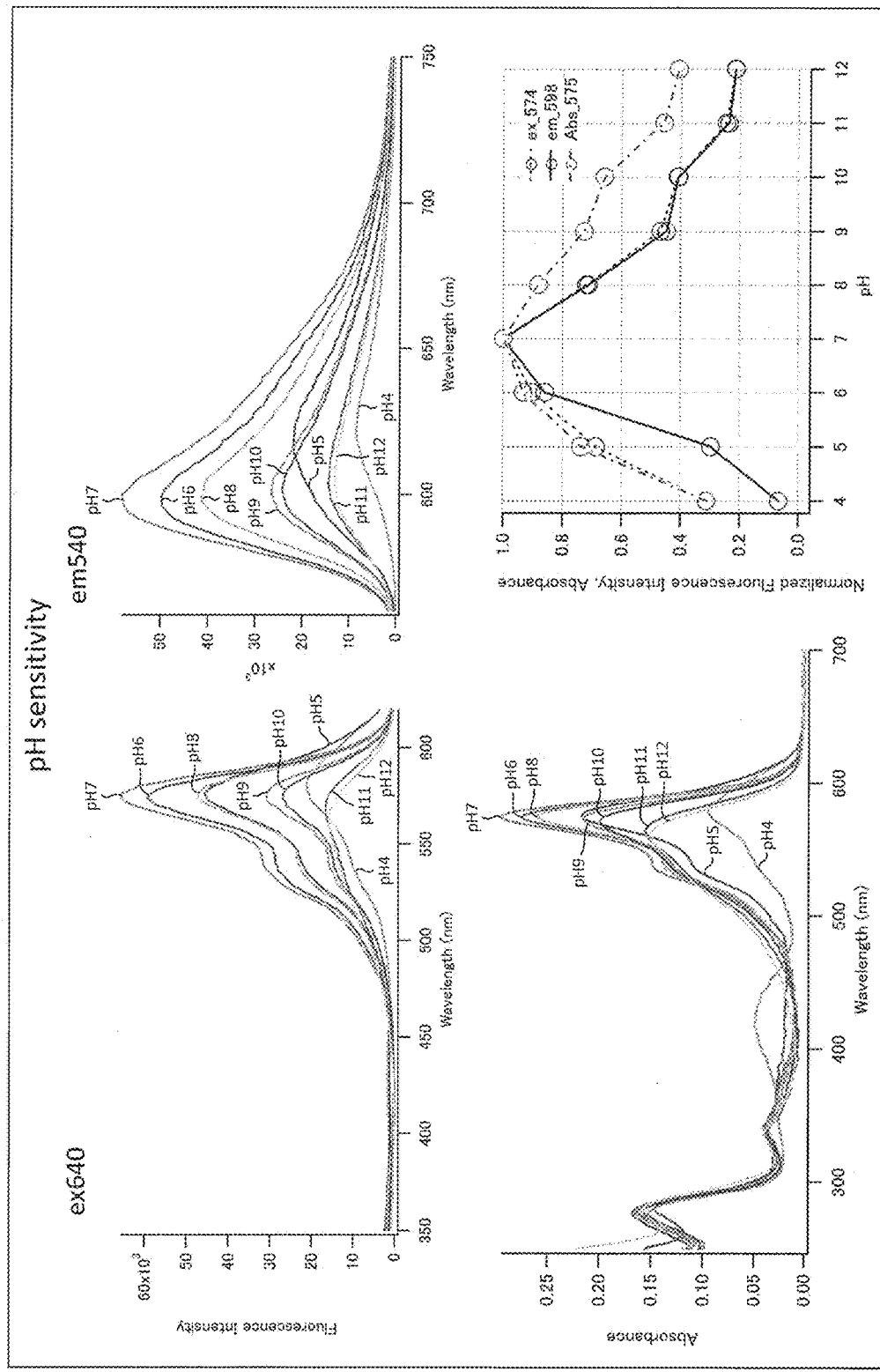
FIG. 8 provides graphs that show the pH sensitivity of mAzalea, which is a protein according to another Example of the present invention.

FIG. 8 shows the pH sensitivity of the fluorescence intensity of mAzalea. The two upper graphs in FIG. 8 show the excitation spectrum (ex640) and fluorescence spectrum (em540) of mAzalea under various pH conditions. The fluorescence intensity of an excitation spectrum shows a value obtained in a case where the wavelength of detection light was fixed at 640 nm. The fluorescence spectrum (em540) shows a value obtained in a case where the wavelength of excitation light was 540 nm.

The lower left graph in FIG. 8 shows the absorption spectrum of mAzalea under various pH conditions. The lower right graph in FIG. 8 shows the absorption (Abs_575) of light having a wavelength of 575 nm, fluorescence intensity of an excitation spectrum, and fluorescence spectrum of mAzalea under various pH conditions. The fluorescence intensity of an excitation spectrum (ex_574) shows a value obtained at 574 nm in a case where the wavelength of detection light was fixed at 640 nm. The fluorescence spectrum (em_598) shows a value obtained at 598 nm in a case where the wavelength of excitation light was fixed at 540 nm.

mAzalea has a stable fluorescence intensity at a pH of 5 or more and 9 or less, in particular at a pH of 6 to 8, with no sensitivity. If the pH is less than 5 or more than 9, the fluorescence intensity, for example, of mAzalea decreases largely. This means that mAzalea, which is a fluorescent protein with a pH sensitivity, is usable as a pH sensor, a pH-dependent switch, or the like.

12. Analysis of Fluorescence Stability of mAzalea (Materials and Method)

Respective genes of mAzalea, mRuby2 (Kredel et al., 2009 PLoS ONE), mCherry, and TagRFP-T were each transfected into a HeLa cell with use of Lipofectamine 2000 reagent. One (1) day after the transfection, the respective light stabilities of the genes were examined for a case where cell immobilization was performed and for a case where cell immobilization was not performed. The measurement conditions were as follows:

<Case Where Cell Immobilization Was Performed>

Immobilizing method: One (1) day after transfection, cells were immobilized with use of 4% PFA on ice over 30 minutes; Buffer: HBSS containing 10 mM of HEPES-NaOH (pH of 7.4); CCD camera: DP30 (produced by Olympus); Fluorescence filter cube: U-MPFP HQ (produced by Olympus), 535-555 nm excitation (BP535-555HQ), 565 nm dichroic mirror (DM565HQ), 570-625 nm fluorescence (BA570-625HQ); Objective lens: ×40 UplanFL N; ND filter: 25%; Binning: 2 (1 second for mcherry only); Exposure time: 15 milliseconds (30 milliseconds for mcherry only); Irradiation interval: 1 minute <Case Where Cell Immobilization Was Not Performed>

Buffer: DMEM/F-12 (produced by Gibco); CCD camera: DP30 (produced by Olympus); Fluorescence filter cube: U-MPFP HQ (produced by Olympus); Objective lens: ×40 UplanFL N; ND filter: 25%; Binning: 2; Exposure time: 40 milliseconds (30 milliseconds for mcherry and TafRFP, 25 milliseconds for mRuby); Irradiation interval: 1 minute (Results)

Figure 9:
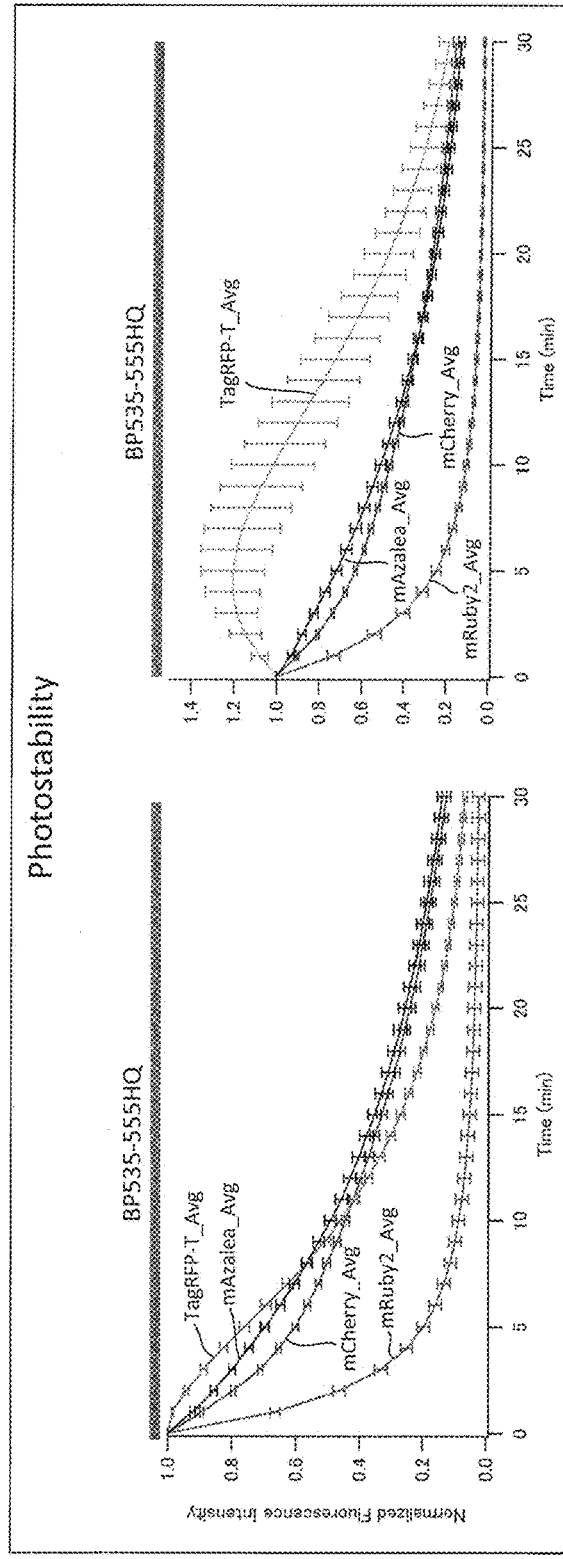
FIG. 9 provides graphs that show the fluorescence stability of mAzalea, which is a protein according to another Example of the present invention, in comparison with the respective fluorescence stabilities of mRuby2, mCherry, TagRFP-T.

FIG. 9 provides graphs that show the respective fluorescence stabilities of mAzalea, mRuby2, mCherry, and TagRFP-T. The left graph in FIG. 9 shows the results for the case where cell immobilization was performed, whereas the right graph shows the results for the case where cell immobilization was not performed. These results indicate that the fluorescence stability of mAzalea is superior to that of mRuby2 and stands comparison with those of the other fluorescent proteins.

13. Local Expression of mAzalea

Figure 10:
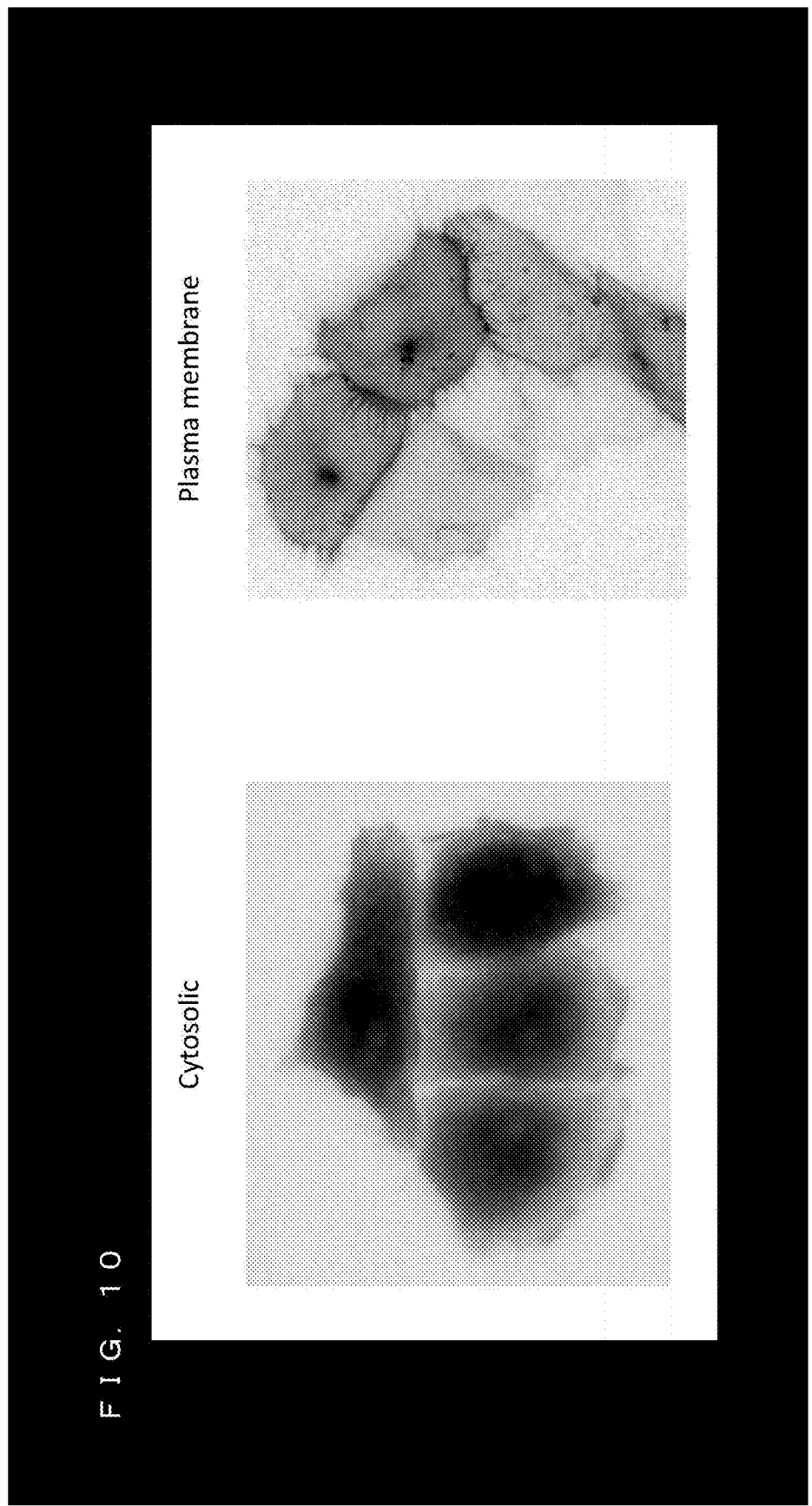
FIG. 10 provides images that show local expression of mAzalea, which is a protein according to another Example of the present invention, in the cytosol of a HeLa cell.
Figure 11:
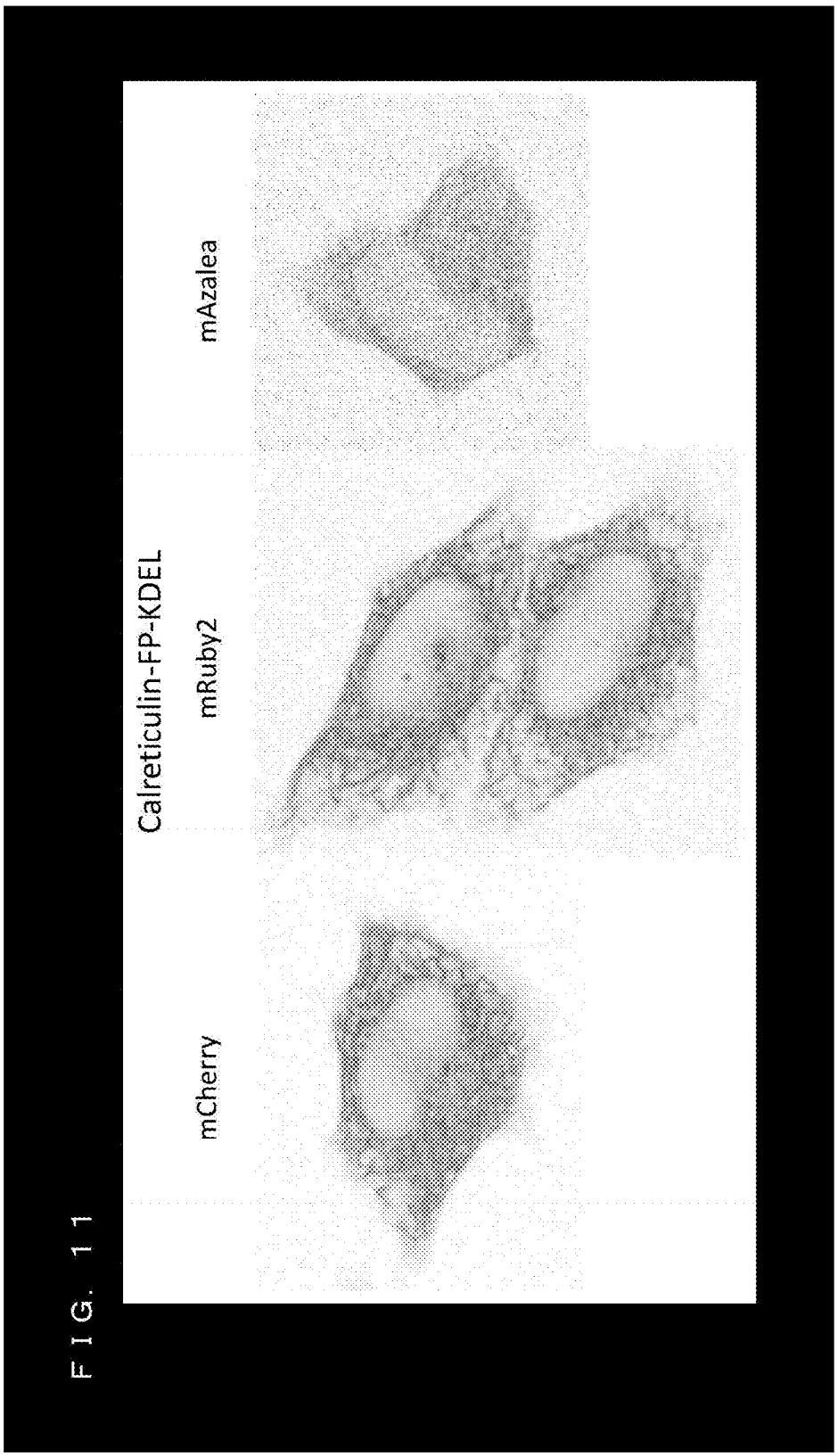
FIG. 11 provides images that show local expression of mAzalea, which is a protein according to another Example of the present invention, in the endoplasmic reticulum of a HeLa cell.
Figure 12:
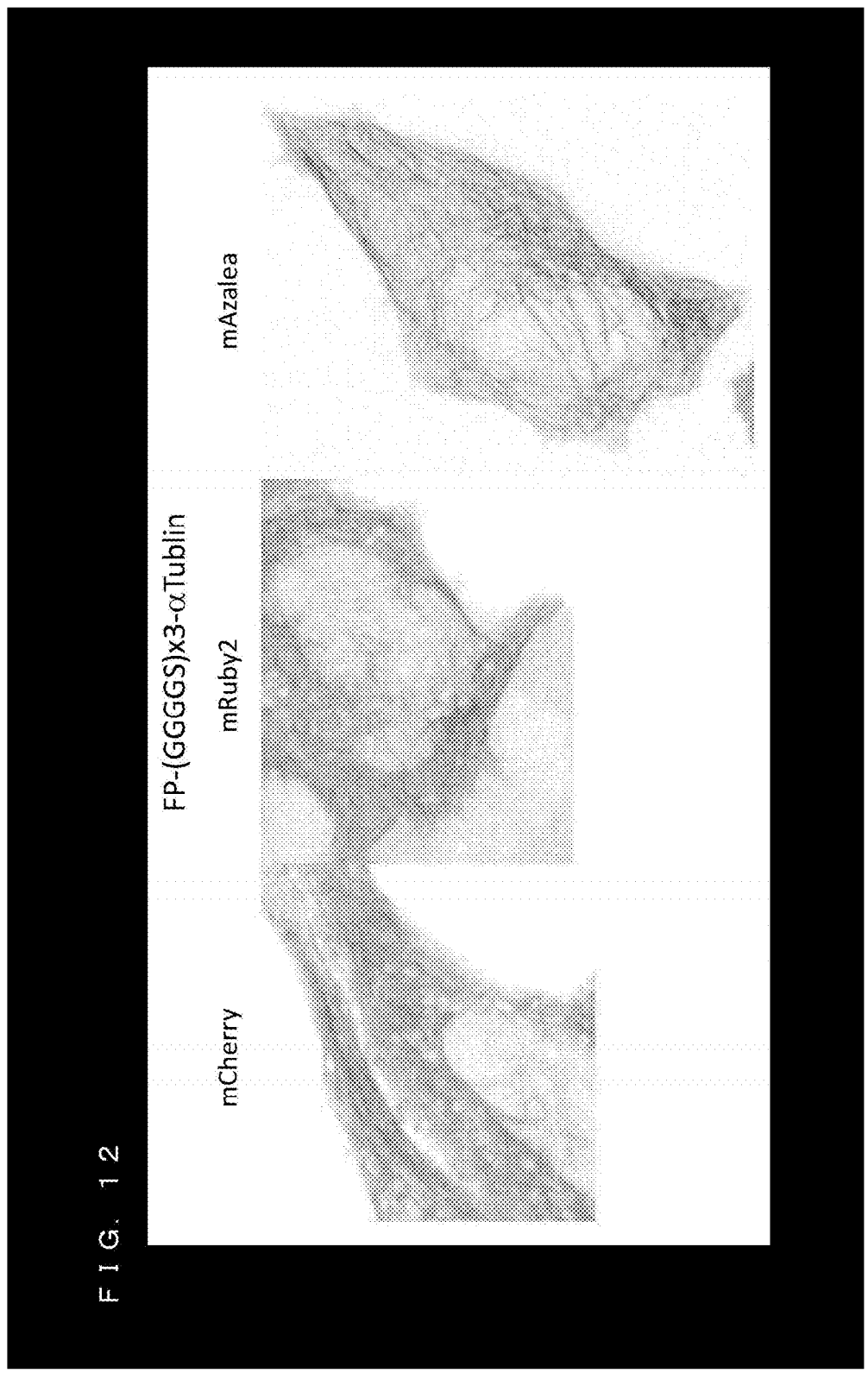
FIG. 12 provides images that show local expression of mAzalea, which is a protein according to another Example of the present invention, in an α-tubulin-containing organ of a HeLa cell.
Figure 13:
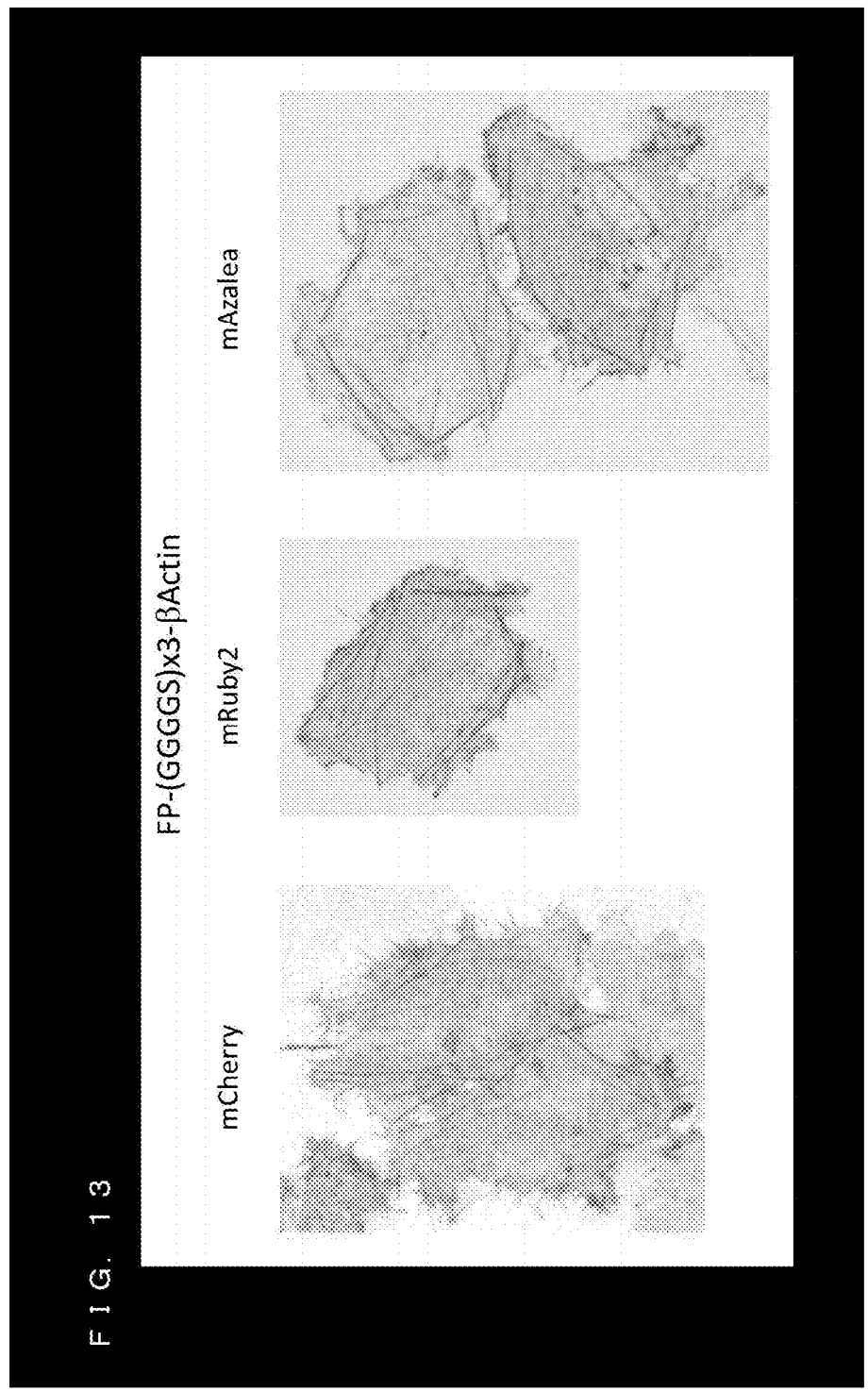
FIG. 13 provides images that show local expression of mAzalea, which is a protein according to another Example of the present invention, in a β-actin-containing organ of a HeLa cell.

Expression of mAzalea was analyzed with use of a HeLa cell, specifically, in its cytosol (left image in FIG. 10), plasma membrane (right image in FIG. 10), endoplasmic reticulum (FIG. 11), organ containing α-tubulin (FIG. 12), and organ containing β-actin (FIG. 13). mAzalea was transfected into HeLa cells with use of Lipofectamine 2000 reagent (Invitrogen). One (1) day later, the cells were observed with use of a fluorescence microscope. Gene constructs used in the transfection were an mAzalea gene (left image in FIG. 10) and Lyn-mAzalea/pcDNA3 (right image in FIG. 10). For FIGS. 11 through 13, a plurality of gene constructs were used that contained respective genes of mAzalea, mRuby2, and mCherry (indicated by FP in FIGS. 11 through 13). Lyn-mAzalea/pcDNA3 is a gene construct in which a membrane-associated Lyn sequence and an mAzalea gene are linked to each other. The gene construct corresponding to FIG. 11 is a gene construct in which calreticulin, FP (fluorescent protein), and KDEL are linked to one another in this order. The gene construct corresponding to FIG. 12 is a gene construct in which FP (fluorescent protein) and α-tubulin are linked to each other with use of a linker (GGGGS)×3. The gene construct corresponding to FIG. 13 is a gene construct in which FP (fluorescent protein) and β-actin are linked to each other with use of a linker (GGGGS)×3.

The results are shown in FIGS. 10 through 13. The measurement conditions were as follows:

<Observation of Cytosol>

Buffer: DMEM/F-12 (produced by Gibco); CCD camera: DP30 (produced by Olympus); Fluorescence filter cube: U-MPFP HQ (produced by Olympus); Objective lens: ×40 UplanFL N; ND filter: 25%; Binning: 2; Exposure time: 35 milliseconds <Observation of Plasma Membrane>

Buffer: 10 mM of HBSS containing HEPES-NaOH (pH of 7.4); CCD camera: DP30 (produced by Olympus); Fluorescence filter cube: U-MPFP HQ (produced by Olympus); Objective lens:×40 UplanFL N; ND filter: 10%; Binning: 2; Exposure time: 400 milliseconds <Observation of Endoplasmic Reticulum>

Microscope: FV1000 (produced by Olympus); Objective lens: ×60 UplanApo W/IR; Scan speed: 2.0 microseconds per pixel; C.A.: 130 µm; Kalman: line,×2; Laser: 543 nm; Fluorescence: 560-660 nm <Observation of Organ Containing α-Tubulin>

Microscope: FV1000 (produced by Olympus); Objective lens: ×60 UplanApo W/IR; Scan speed: 4.0 microseconds per pixel; C.A.: 120 µm; Kalman: line,×4; Laser: 543 nm; Fluorescence: 560-660 nm <Observation of Organ Containing β Actin>

Microscope: FV1000 (produced by Olympus); Objective lens: ×60 UplanApo W/IR; Scan speed: 2.0 microseconds per pixel; C.A.: 130 µm; Kalman: line,×2; Laser: 543 nm; Fluorescence: 560-660 nm (Results)

As illustrated in FIGS. 10 through 13, mAzalea was found to function as a fluorescence marker that is expressed locally at a target position of a HeLa cell.

14. Maturation Rate of mAzalea

Figure 14:
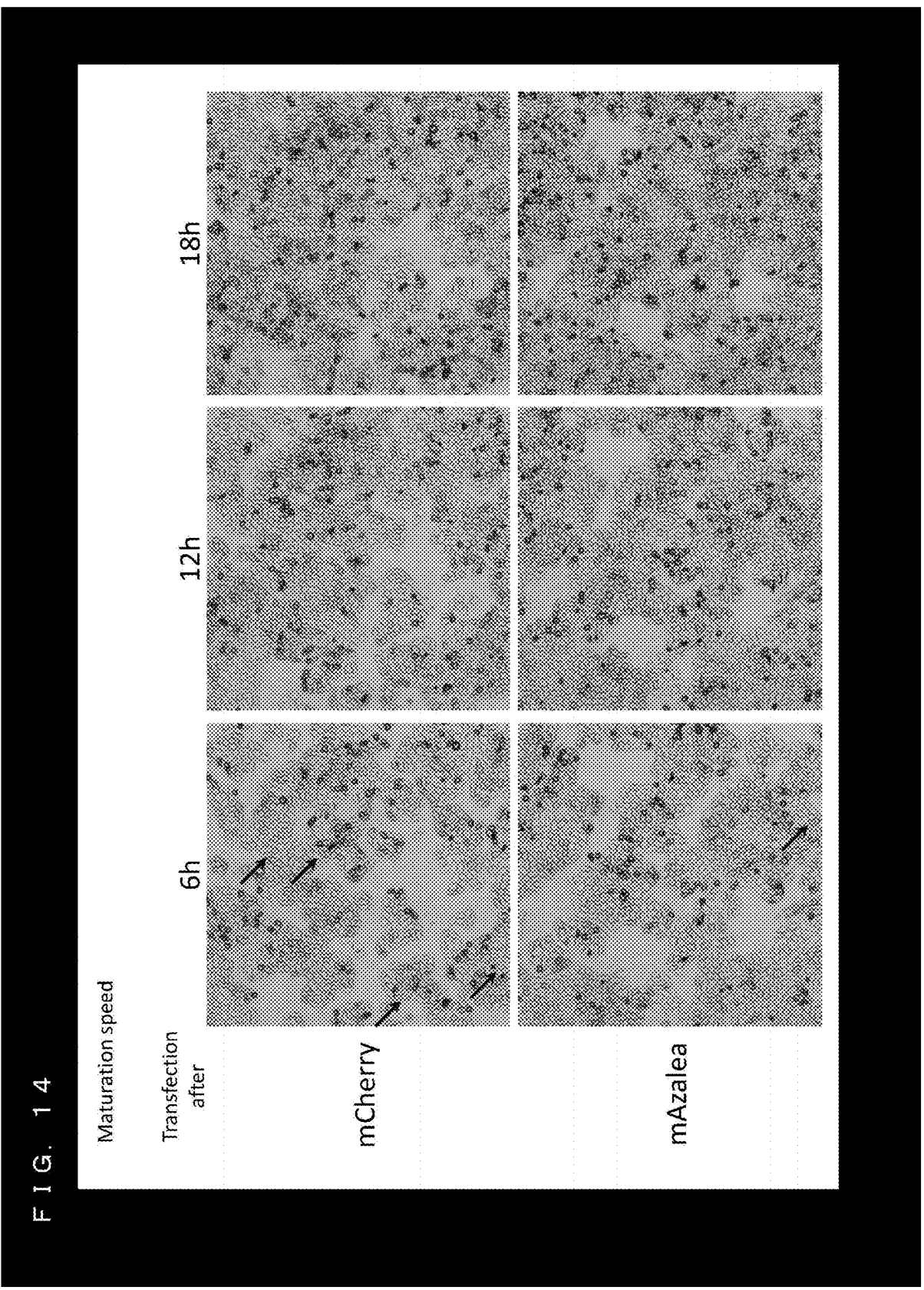
FIG. 14 provides images that show the results of comparing how early mAzalea, which is a protein according to another Example of the present invention, starts to light as compared with mCherry.

Next, how early mAzalea starts to light was compared with the case of mCherry. Respective genes of mAzalea and mCherry were transfected into HeLa cells (HeLa S3). Then, the fluorescence emission was examined after 6 hours, 12 hours, and 18 hours of culture of the HeLa cells. As indicated by the results shown in FIG. 14, how early mAzalea starts to light was equivalent to that for mCherry.

HeLa cell transfection condition: 1 µg of plasmid was transfected with use of FuGENE (registered trademark) HD.

HeLa cell culture condition: The medium was a DMEM medium to which 10% FBS had been added. The culture was performed with use of FV10i, a culture device for a microscope, at 37° C. in the presence of carbon dioxide at a concentration 5%.

Fluorescence emission observation condition: Laser: 559 nm_7.5%, PMT: 40%, em: 570-670 nm, C.A.: 300 um Objective lens (Obj): UPlanSApo 10×, Scan speed: 2 microseconds per pixel Image size: 512×512, Zoom:×1, Kalman: line×2

Interval: 15 min

15. Production and Analysis of mAzalea-Based Mutant Protein

In the amino acid sequence of mAzalea described under [9. Analysis of Other Mutants] above, isoleucine at amino acid 85 was replaced with leucine, and tyrosine at amino acid 176 was replaced with methionine. This mutant protein produced was named mAzalea_B5. A site-specific amino acid mutation was introduced by use of an mAzalea gene sequence as a template. mAzalea_B5 had an amino acid sequence represented by SEQ ID NO. 18, and the coding region of a gene encoding mAzalea_B5 had a base sequence represented by SEQ ID NO. 19.

Next, to analyze the fluorescence property of mAzalea_B5 obtained, measurements of the absorption spectrum, the fluorescence spectrum, and the quantum yield were performed. The protein was suspended with use of a spectro photometer (Hitachi High-Technologies Corporation) to have 40 µM in 50 mM of HEPES-NaOH (pH of 7.4), and the absorption spectrum was then measured. Further, the molar extinction coefficient was calculated at the maximum absorption wavelength. The molar extinction coefficient was calculated under conditions similar to those for the case of mAzalea. mAzalea_B5 (fluorescent protein) was suspended with use of SynergyMx (BioTek) to have 2 µM in 50 mM of HEPES-NaOH (pH of 7.4), and the fluorescence spectrum was then measured. Further, mAzalea was suspended with use of an absolute PL quantum yield measuring system (Hamamatsu Photonics K.K.) to have 2 µM in 50 mM of HEPES-NaOH (pH of 7.4), and the quantum yield was then measured. The protein was suspended to have 2 µM so as to be adjusted to have an absorption value of 0.1 at 540 nm. The results are shown in the left side of FIG. 15.

16. Analysis of pH Sensitivity of mAzalea_B5

(Materials and Method)

For a purified protein of each of mAzalea and mAzalea_B5, the fluorescence intensity was measured with use of SynergyMx (Biotek) in 50 mM of $CH_3COONa$—$CH_3COOH$ (pH of 4.0 and pH of 5.0), 50 mM of $KH_2PO_4$—NaOH (pH of 6.0), 50 mM of HEPES-NaOH (pH of 7.0), 50 mM of Tricine-NaOH (pH of 8.0), 50 mM of Glycine-NaOH (pH of 9.0 and pH of 10.0), 50 mM of $Na_2HPO_4$—NaOH (pH of 11.0), and 50 mM of 0.2M KCl-0.2M NaOH (pH of 12.0). The measurement values obtained were normalized on the basis of the largest value. Further, the absorption spectrum was also measured with use of a spectro photometer (Hitachi High-Technologies Corporation).

(Results)

Figure 15:
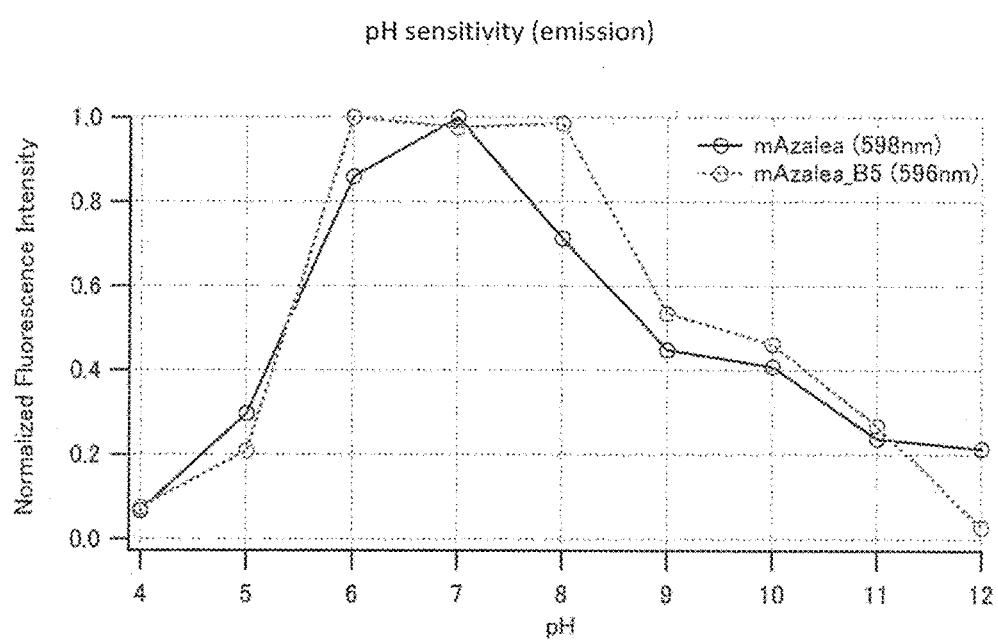
FIG. 15 is a graph that shows the pH sensitivity of mAzalea_B5, which is a protein according to still another Example of the present invention.

The right graph in FIG. 15 shows the respective fluorescence spectrums of mAzalea and mAzalea_B5 under various pH conditions. The fluorescence spectrum for mAzalea shows a value obtained at 598 nm in a case where the wavelength of excitation light was fixed at 540 nm. The fluorescence spectrum for mAzalea_B5 shows a value obtained at 596 nm in a case where the wavelength of excitation light was fixed at 540 nm.

As a result of analyzing the fluorescence property, mAzalea B5 has the following main properties at a pH 7.4:

Absorption peak (nm): 574 Maximum excitation wavelength (nm): 574

Maximum fluorescence wavelength (nm): 596 (red)

Molar extinction coefficient ($M^{-1}$ $cm^{-1}$): 103700

Quantum yield (%): 58 mAzalea_B5 has a more stable fluorescence intensity than mAzalea at a pH of 5 or more and 9 or less, in particular at a pH of 6 to 8, with no sensitivity. If the pH is less than 5 or more than 9, the fluorescence intensity of mAzalea_B5 decreases significantly. This means that mAzalea_B5, which is a fluorescent protein with a pH sensitivity, is usable as a pH sensor, a pH-dependent switch, or the like.

17. Analysis of Fluorescence Stability of mAzalea_B5

Respective genes of mAzalea and mAzalea_B5 were each transfected into a HeLa cell with use of Lipofectamine 2000 reagent (Invitrogen). One (1) day later, the cells were observed with use of a fluorescence microscope.

Figure 16:
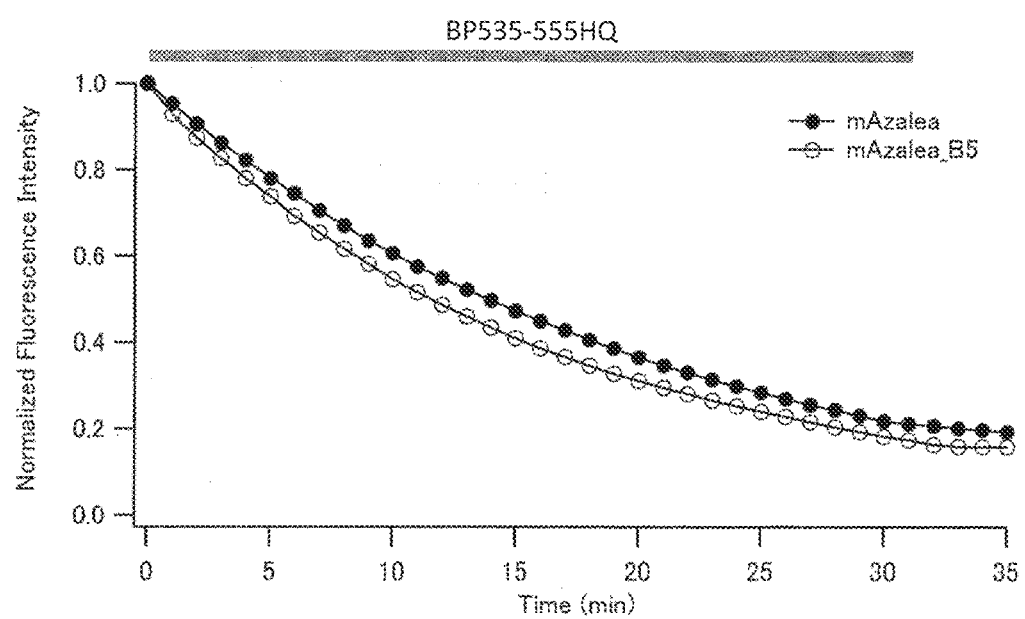
FIG. 16 is a graph that shows the light stability of mAzalea_B5, which is a protein according to still another Example of the present invention.

The results are shown in FIG. 16. The measurement conditions were as follows:

Buffer: 10 mM of HBSS containing HEPES-NaOH (pH of 7.4); CCD camera: CoolSNAP HQ; Fluorescence filter cube: U-MPFP HQ (produced by Olympus); Objective lens: ×40 UplanFL N; ND filter: 30%; Binning: 1; Exposure time: 25 milliseconds; Irradiation interval: 1 minute The measurements confirmed that the respective fluorescence stabilities of mAzalea and mAzalea_B5 were equivalent to each other.

18. Local Expression of mAzalea_B5

Expression of mAzalea and mAzalea_B5 was analyzed with use of a HeLa cell, specifically, in its endoplasmic reticulum. mAzalea and mAzalea_B5 were each transfected into HeLa cells with use of Lipofectamine 2000 reagent (Invitrogen). One (1) day later, the cells were observed with use of a fluorescence microscope. The gene construct used in the transfection was a gene construct in which calreticulin, FP, and KDEL are linked to one another in this order, where FP indicates an mAzalea gene or mAzalea_B5 gene.

The results are shown in FIG. 17. The measurement conditions were as follows:

Microscope: FV1000 (produced by Olympus); Objective lens: ×60 UplanApo W/IR; Scan speed: 4.0 microseconds per pixel; C.A.: 120 μm; Kalman: line,×4; Laser: 543 nm (30%); Fluorescence: 560-660 nm, PMT: 770 V (Results)

As illustrated in FIG. 17, mAzalea_B5 was found to function more excellently than mAzalea as a fluorescence marker that is expressed locally at the endoplasmic reticulum of a HeLa cell.

The present invention is not limited to the description of the embodiments and examples above, but may be altered by a skilled person within the scope of the claims. Any embodiment based on a proper combination of technical means disclosed in different embodiments is encompassed in the technical scope of the present invention. Further, the entire content of each reference document cited in the present specification is incorporated in the present specification by reference.

INDUSTRIAL APPLICABILITY

An example fluorescent protein according to the present invention has properties such as an excellent quantum yield. The fluorescent protein is therefore useful in such fields as the biochemical analysis field and medical field as, for example, a fluorescent label for analyzing the expression pattern of a target gene or a fluorescent label for use in screening candidate medical compounds.

SEQUENCE LISTING

RK14145PCT_sequence.txt

The invention claimed is:

1. A polypeptide having a fluorescence property, the polypeptide being defined in any one of (1) to (3) below:
   (1) A polypeptide having the amino acid sequence represented by SEQ ID NO. 1 or NO. 2,
   (2) A polypeptide having a sequence identity of 90% or more with respect to the amino acid sequence represented by SEQ ID NO. 1 or NO. 2, and
   (3) A polypeptide that has an amino acid sequence in which at least one of amino acids 85, 151, and 176 of the amino acid sequence represented by SEQ ID NO. 1 or NO. 2 has been replaced with another amino acid(s) and which has a sequence identity of 90% or more with respect to the amino acid sequence represented by SEQ ID NO. 1 or NO. 2.

2. The polypeptide according to claim 1, wherein the polypeptide has a fluorescence quantum yield Φ of 0.4 or more.

3. A fusion polypeptide comprising:
   the polypeptide according to claim 1; and
   another polypeptide.

4. A method for fluorescence observation, the method comprising the steps of:
   producing, in a cell, the polypeptide according to claim 1; and
   observing fluorescence from the polypeptide.

5. A kit comprising:
   the polypeptide according to claim 1.

6. The polypeptide according to claim 1, wherein the polypeptide is as defined in (1) or (2) below:
   (1) A polypeptide having a sequence identity of 95% or more with respect to the amino acid sequence represented by SEQ ID NO. 1 or NO. 2, and
   (2) A polypeptide having an amino acid sequence in which two or three of amino acids 85, 151, and 176 of the amino acid sequence represented by SEQ ID NO. 1 or NO. 2 has been replaced with another amino acid(s) and, which has a sequence identity of 90% or more with respect to the amino acid sequence represented by SEQ ID NO. 1 or NO. 2.

7. A polynucleotide defined in any one of (1) to (3) below:
   (1) A polynucleotide encoding a polypeptide having the amino acid sequence represented by SEQ ID NO. 1 or NO. 2,
   (2) A polynucleotide encoding a polypeptide that has a sequence identity of 90% or more with respect to the amino acid sequence represented by SEQ ID NO. 1 or NO. 2 and that has a fluorescence property, and
   (3) A polynucleotide encoding a polypeptide that has an amino acid sequence in which at least one of amino acids 85, 151, and 176 of the amino acid sequence represented by SEQ ID NO. 1 or NO. 2 has been replaced with another amino acid(s) and which has a sequence identity of 90% or more with respect to the amino acid sequence represented by SEQ ID NO. 1 or NO. 2 and that has a fluorescence property.

8. An expression cassette comprising:
   (a) an expression regulatory region functional in an expression host; and
   (b) the polynucleotide according to claim 7.

9. A vector comprising:
   the polynucleotide according to claim 7.

10. A transformant that is a cell comprising: the polynucleotide according to claim 7.

11. A method for producing a transformant that is a cell including, in a cell, all or part of a polynucleotide according to claim 7,
    the method comprising the step of introducing, into a cell, the polynucleotide according to claim 7.

12. A transformant produced by the method according to claim 11 or progeny of the transformant.

13. A kit comprising:
    the polynucleotide according to claim 7.

* * * * *